United States Patent
Kawazoe et al.

(10) Patent No.: US 8,343,125 B2
(45) Date of Patent: Jan. 1, 2013

(54) ABSORBENT ARTICLE

(75) Inventors: Masashi Kawazoe, Tochigi (JP); Takuya Kouta, Tochigi (JP); Takeshi Miyamura, Tochigi (JP)

(73) Assignee: Kao Corporation, Tokyo (JP)

( * ) Notice: Subject to any disclaimer, the term of this patent is extended or adjusted under 35 U.S.C. 154(b) by 377 days.

(21) Appl. No.: 12/739,135

(22) PCT Filed: Dec. 11, 2008

(86) PCT No.: PCT/JP2008/072499
§ 371 (c)(1),
(2), (4) Date: Apr. 21, 2010

(87) PCT Pub. No.: WO2009/081744
PCT Pub. Date: Jul. 2, 2009

(65) Prior Publication Data
US 2010/0262108 A1 Oct. 14, 2010

(30) Foreign Application Priority Data

| Dec. 25, 2007 | (JP) | 2007-332419 |
| Apr. 15, 2008 | (JP) | 2008-105867 |
| Nov. 25, 2008 | (JP) | 2008-299999 |
| Nov. 25, 2008 | (JP) | 2008-300000 |

(51) Int. Cl.
*A61F 13/15* (2006.01)
(52) U.S. Cl. .......... 604/385.101; 604/378; 604/380; 604/383; 604/385.01
(58) Field of Classification Search .......... 604/378, 604/380, 383, 385.01, 385.101
See application file for complete search history.

(56) References Cited

U.S. PATENT DOCUMENTS

| 6,203,654 B1 | 3/2001 | McFall et al. |
| 2001/0014797 A1 | 8/2001 | Suzuki et al. |

FOREIGN PATENT DOCUMENTS

| JP | 7-155596 A | 6/1995 |
| JP | 10-75978 A | 3/1998 |
| JP | 2001-46435 A | 2/2001 |
| JP | 2001-190581 A | 7/2001 |
| JP | 2003-103677 A | 4/2003 |
| JP | 2003-521947 A | 7/2003 |

OTHER PUBLICATIONS

Notification of the First Office Action dated May 3, 2012 for Chinese Application No. 200880117615.5 with English translation.

*Primary Examiner* — Jacqueline F. Stephens
(74) *Attorney, Agent, or Firm* — Birch, Stewart, Kolasch & Birch, LLP

(57) ABSTRACT

An absorbent article (100) includes a topsheet (101), a backsheet (102), and an absorbent core (10). The absorbent core (10) includes a number of discretely and independently arranged absorbent members (30) located across a planar direction of the article (100). An intermediate sheet (20) is disposed between the topsheet (101) and the absorbent core (10) or between the backsheet (102) and the absorbent core (10). The absorbent members (30) are fixed to the intermediate sheet (20). It is preferable that an absorption rate of physiological saline solution measured by D/W method of each of the topsheet (101), the intermediate sheet (20), and the absorbent core (10) satisfies the following relationship: the topsheet (101)<the intermediate sheet (20)<the absorbent core (10).

13 Claims, 11 Drawing Sheets

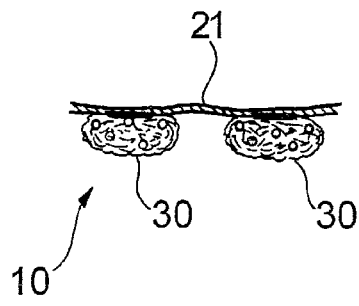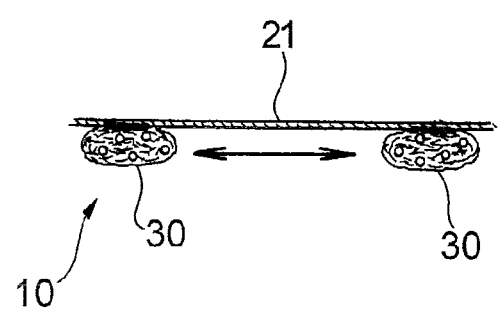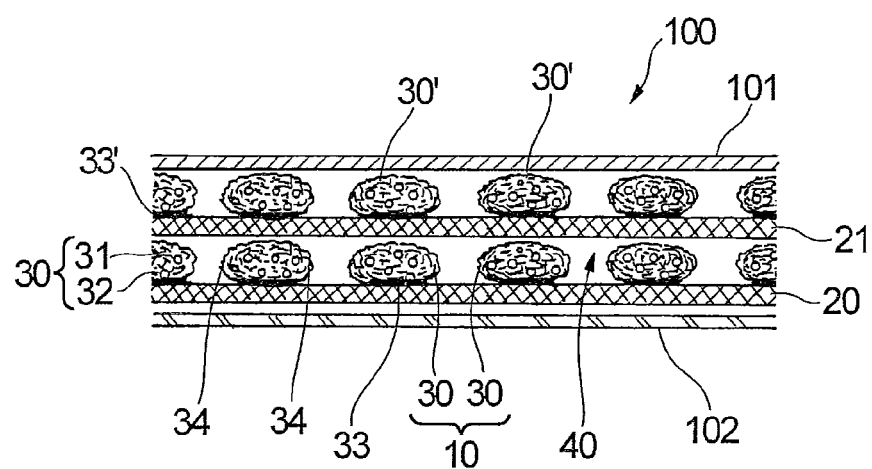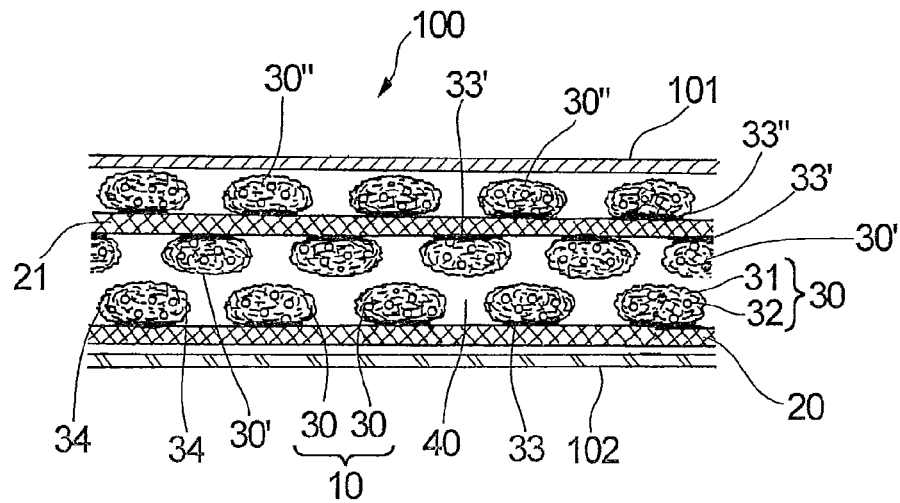

ABSORBENT ARTICLE

TECHNICAL FIELD

The present invention relates to an absorbent article such as a sanitary napkin and a disposable diaper.

BACKGROUND ART

A known absorbent core for an absorbent article has a side that faces the absorbent article's topsheet formed into a projecting-and-depressed shape. Patent Document 1, for example, discloses a sheet-like conjugate absorbent core that consists of a conjugate core made by superposing a superabsorbent core sheet on a liquid-impermeable sheet. The liquid-impermeable sheet and the superabsorbent core sheet are joined together at a plurality of long-and-narrow joining portions that are parallel to one another, and channels are formed between the liquid-impermeable sheet and the superabsorbent core sheet in the respective spaces between adjacent joining portions.

Further, Patent Document 2 discloses an absorbent core, which consists of a laminate of a nonwoven fabric layer and a fibrous web layer, for an absorbent article. The laminate includes first network regions that are thin and have high density, and second network regions that are thick and have a lower density than the first network regions. The surface of the fibrous web layer is bulky and has projections and depressions. The first network regions are arranged in the form of bands intersecting one another, whereas the second network regions are provided as partitioned layers surrounded by the first network regions.

These absorbent cores come into contact with the topsheet only at their projections. Therefore, when fluid is excreted on the topsheet, the spaces between the projections provide improved fluid permeability for low-viscosity fluid such as urine. However, for high-viscosity fluid such as menstrual blood, fluid may be transferred through portions in contact with the projections, but is less likely to be transferred at portions that are not in contact with the projections. This may result in fluid residue on the topsheet and tends to deteriorate the dry feel of the topsheet.

Further, in cases where high-viscosity fluid such as soft feces is excreted on an absorbent article having such an absorbent core, the high-viscosity fluid is retained in the depressions between the projections of the absorbent core. Since the high-viscosity fluid is retained in the depressions in its as-is viscous state, the retainability of the fluid in the absorbent core is poor, causing the fluid to flow in the absorbent core due to a wearer's movement. Furthermore, in cases where body pressure etc. is applied on the article, the high-viscosity fluid is prone to cause wet-back from the topsheet.

Patent Document 1: JP 7-155596A
Patent Document 2: JP 2003-103677A

DISCLOSURE OF THE INVENTION

The present invention provides an absorbent article comprising a topsheet that is adapted to be located proximal to a wearer's skin, a backsheet that is adapted to be located distal to the wearer's skin, and an absorbent core disposed between the topsheet and the backsheet. The absorbent core comprises a number of discretely and independently arranged absorbent members which are located across a planar direction of the article. An intermediate sheet is disposed between the topsheet and the absorbent core or between the backsheet and the absorbent core. The absorbent members are fixed to the intermediate sheet.

BRIEF DESCRIPTION OF THE DRAWINGS

FIGS. 8(a) to 8(c) are process flow diagrams sequentially showing a process for producing the absorbent members of FIG. 2.

FIGS. 19(a) and 19(b) are schematic diagrams respectively showing states of the absorbent members when a base sheet of the absorbent article of FIG. 18 is contracted and stretched.

FIG. 20 is a schematic diagram (corresponding to FIG. 16) showing a cross-sectional structure of an absorbent article according to a seventh embodiment of the present invention taken along the width direction in the lengthwise middle region of the absorbent article.

FIG. 21 is a schematic diagram (corresponding to FIG. 16) showing a cross-sectional structure of an absorbent article according to an eighth embodiment of the present invention taken along the width direction in the lengthwise middle region of the absorbent article.

DETAILED DESCRIPTION OF THE INVENTION

Figure 1:
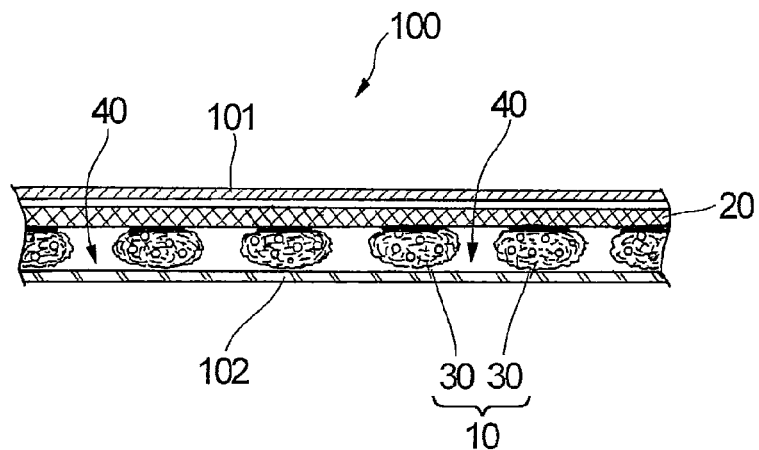
FIG. 1 is a schematic diagram showing a cross-sectional structure of a first embodiment of an absorbent article of the present invention taken along the width direction in the lengthwise middle region of the absorbent article.

The present invention is described below according to preferred embodiments thereof with reference to the drawings. FIG. 1 schematically shows a cross-sectional structure of a first embodiment of an absorbent article of the present invention taken along the width direction in the lengthwise middle region of the absorbent article. Although not shown in the drawings, the cross-sectional structure taken along the length direction in the widthwise middle region is substantially the same as FIG. 1. The absorbent article (also referred to simply as "article" hereinafter) 100 has a topsheet 101 that is adapted to be located proximal to a wearer's skin and that faces the wearer's skin and a backsheet 102 that is adapted to be located distal to the wearer's skin and that faces the underwear. An absorbent core 10 is disposed between the sheets 101 and 102. A pair of three-dimensional guards (not shown) may be disposed on the right and left sides on the topsheet 101, as necessary.

The same type of material that is usually employed in the present technical field can be used as the topsheet 101 and the backsheet 102. As the topsheet 101, it is possible to use, for example, a nonwoven fabric or a perforated film having liquid permeability. As the backsheet 102, it is possible to use, for example, a liquid-impermeable film or a nonwoven fabric that is hardly permeable to liquid. The liquid-impermeable film may be moisture permeable.

The absorbent core 10 has a group of absorbent members 30 (hereinafter referred to as "absorbent member group") which are discretely and independently arranged across the planar direction of the article 100. An intermediate sheet 20 having functions of drawing in and diffusing fluid excreted on the article 100 is disposed between the absorbent core 10 and the topsheet 101. Substantially the entire region of the upper surface of the intermediate sheet 20 is in planar contact with the lower surface of the topsheet 101. Note that the term "across the planar direction" does not necessarily have to mean that the absorbent members 30 exist throughout the entire surface of the absorbent article, but encompasses, as necessary, a state where regions with absorbent members 30 and regions without absorbent members 30 exist in part.

Figure 2:
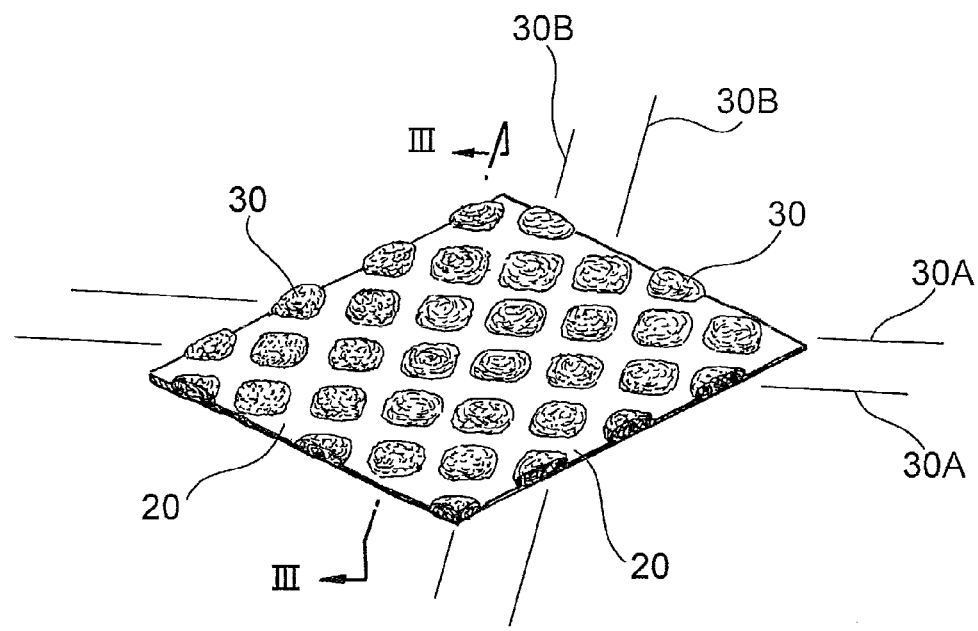
FIG. 2 is a perspective of absorbent members and an intermediate sheet of the absorbent article of FIG. 1 as viewed from the side of the absorbent members.
Figure 3:
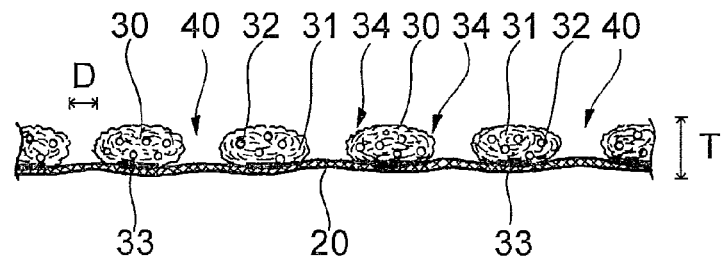
FIG. 3 is a cross-sectional view taken along line III-III of FIG. 2.

FIG. 2 shows a perspective of the absorbent members 30 and the intermediate sheet 20 of the article 100 as viewed from the side of the absorbent members. FIG. 3 is a cross-sectional view taken along line III-III of FIG. 2. Note that FIGS. 2 and 3 show the absorbent members 30 and the intermediate sheet 20 of the absorbent article 100 of FIG. 1 turned upside down. The absorbent members 30 are parts capable of absorbing and retaining liquid. There is no particular limitation to the type of material constituting the absorbent members 30, as long as they are capable of absorbing and retaining liquid. As shown, for example, in FIG. 3, the absorbent member 30 is made of a homogeneous mixture of a fibrous material 31 and superabsorbent polymer 32. In this example, the superabsorbent polymer 32 is retained within the fibrous material 31.

When viewed from above, the absorbent member 30 has the shape of a circle or a rectangle whose corners are rounded and whose sides each take the form of a gentle curve slightly convex outward. The plan-view shape of the absorbent member 30, however, is not limited to the above. For example, the plan-view shape of the absorbent member 30 may be a square, a rectangle, or a rhombus. Further, two or more of these shapes may be used in combination.

The absorbent members 30 are disposed on the intermediate sheet 20 across the planar direction thereof according to a regular, scattered pattern. More specifically, the absorbent members 30 are disposed so as to be lined up in a plurality of first rows 30A and a plurality of second rows 30B intersecting with the first rows 30A. The surface (lower surface) of the intermediate sheet 20 is exposed between adjacent absorbent members 30. Thus, spaces 40 are formed between adjacent absorbent members 30, each space 40 including the exposed section of the intermediate sheet 20. The spaces 40 are designed to have a capacity, width, and/or height allowing permeation of liquid having passed through the topsheet 101 as well as flow of liquid in the absorbent core 10.

The absorbent members 30 are fixed to the intermediate sheet 20 through respective fixing points 33. For convenience' sake, the fixing points 33 are shown with bold lines in FIG. 3. The fixing points 33 are formed, for example, through ultrasonic embossing or with an adhesive such as a hot melt adhesive. In these cases, it is not necessary to fix all of the absorbent members 30 to the intermediate sheet 20. For example, it is preferable to apply fixing with the fixing points 33 in portions where the absorbent core 10 is significantly deformed due to a wearer's movement. Further, the lower surface of each absorbent member 30 may be fixed to the upper surface of the backsheet 102, but does not have to be fixed thereto. In either case, the lower surface of each absorbent member 30 is in contact with the upper surface of the backsheet 102.

Figure 4:
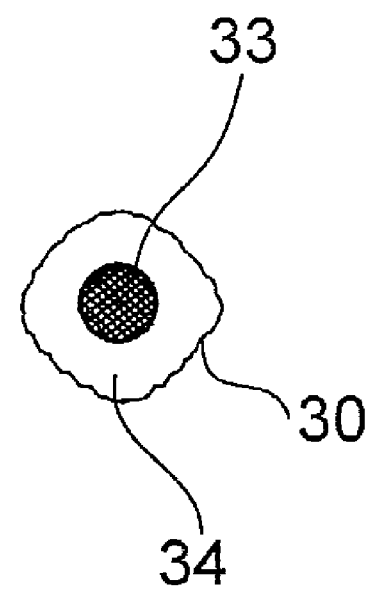
FIG. 4 is an explanatory diagram showing a positional relationship between an absorbent member and a fixing point when viewing the absorbent member of FIG. 2 from above.

FIG. 4 shows a positional relationship between the absorbent member 30 and the fixing point 33 when the absorbent core 10 is viewed from above. As is clearly seen from FIGS. 3 and 4, the contour of the fixing point 33 is encompassed within the contour of the absorbent member 30 when viewed from above. Also, the absorbent members 30 are located on the respective fixing points 33. Thus, the absorbent member 30 is shaped so that it has an overhanging projection 34 (hereinafter referred to as an overhang 34) outwardly projecting from the fixing point 33 in the planar direction. The overhang 34 may be spaced from the intermediate sheet 20, or the upper surface of the overhang 34 may be in contact with the lower surface of the intermediate sheet 20. (Note that FIG. 3 is upside down from FIG. 1.) In either case, the absorbent member 30 is not fixed to the intermediate sheet 20 at its overhang 34. Providing an overhang 34 to each absorbent member 30 allows the total area of the fixing points 33 to be minimized which cause deterioration in the draping property of the intermediate sheet 20 due to formation of the fixing points 33. Thus, it is possible to provide an absorbent article 100 that has a superior draping property and that allows the absorbency to be improved by increasing the total area of the absorbent members 30.

Note that, although the fixing point 33 has a circular plan-view shape in FIG. 4, the plan-view shape thereof is not limited thereto. For example, the plan-view shape of the fixing point 33 may be a square, a rectangle, or a rhombus. Further, two or more of these shapes may be used in combination. Furthermore, the combination of the shapes of the fixing point 33 and the absorbent member 30 as viewed from above is not particularly limited to that shown in FIG. 4.

From the standpoint of achieving both superior absorbency and draping property, it is preferable that the plan-view area of each absorbent member 30 is from 10 to 900 mm$^2$, and more preferably from 50 to 450 mm$^2$. Further, from the standpoint of providing superior comfort to the wearer and the standpoint of making the article 100 fit to the wearer's body by reducing the rigidity of the absorbent core 10, it is preferable that the sum of the thickness of the absorbent member 30 and the thickness of the intermediate sheet 20 where an absorbent member 30 exists is from 1 to 10 mm, and more preferably from 1.2 to 5 mm. The area and thickness T of the absorbent member 30 can be adjusted by controlling the conditions for producing the absorbent core 10, which are described further below.

Further, from the standpoint of providing sufficient strength so that the absorbent member 30 does not fall off from the intermediate sheet 20 due to deformation caused by the wearer's movement etc., it is preferable that the area of each fixing point 33 for fixing the absorbent member 30 to the intermediate sheet 20 is from 1 to 100 mm$^2$, and more preferably from 5 to 50 mm$^2$, provided that the area of the fixing point is smaller than that of the absorbent member 30 when viewed from above. Furthermore, from the standpoint of maintaining the draping property of the intermediate sheet 20, it is preferable that the total sum of the area of the fixing points 33, as viewed from above, is from 5% to 95%, and more preferably from 20% to 70%, with respect to the area of the intermediate sheet 20.

The distance D (see FIG. 3) between adjacent absorbent members 30 has an influence on the capacity of the space 40 and thus the flowability of liquid through the space 40. From this standpoint, it is preferable that the distance D is from 0.2 to 5 mm, and more preferably from 0.5 to 3 mm. The distance D can be adjusted by controlling the conditions for producing the absorbent core 10, which are described further below. Note that, if there are a plurality of other absorbent members 30 around a certain absorbent member 30 and the distance D between that certain absorbent member 30 and another one of the absorbent members 30 differs depending on the other absorbent member 30, then the minimum distance D is regarded as the "distance between adjacent absorbent members 30".

The material constituting the absorbent member 30 is not particularly limited, and fibrous materials, porous elements, and combinations thereof may be used. Examples of fibrous materials that may be used include: natural fibers such as wood pulp, cotton, and hemp; single fibers made of synthetic resin including e.g. polyolefin-based resin such as polyethylene and polypropylene, polyester-based resin such as polyethylene terephthalate, and polyvinyl alcohol resin; conjugate fibers including two or more types of these resins; and semi-synthetic fibers such as acetate and rayon. In cases where a fiber made of synthetic resin is to be used, it may be a heat-shrinkable fiber that deforms by heat. For example, it is possible to employ a fiber whose fineness becomes thick but whose fiber length becomes short by heat, or a fiber whose fineness hardly changes by heat but whose apparent occupied length (the apparent length that the fiber occupies) decreases due to it deforming into a coil. Examples of porous elements that may be used include sponge, nonwoven fabrics, and an aggregate of superabsorbent polymer.

Preferable polymers for the superabsorbent polymer 32 contained in the absorbent member 30 include those that can absorb and retain body fluid of an amount five times or more of its own weight and that can gel. There is no particularly preferable shape therefor, and the polymer may be spherical, clump-like, botryoidal, powdered, or fibrous. Particulate polymers having a size of 1 to 1000 μm, and more preferably 10 to 500 μm, are preferred. Examples of such superabsorbent polymers may include starch, cross-linked carboxyl methyl cellulose, polymers or copolymers of acrylic acid or alkali metal salts thereof, polyacrylic acid or salts thereof, and graft polymers of polyacrylic acid salts. Preferable polyacrylic acid salts that can be used are sodium salts. It is also possible to preferably use copolymers in which a comonomer, such as maleic acid, itaconic acid, acrylamide, 2-acrylamido-2-methylpropane sulfonic acid, 2-(meth)acryloyl ethane sulfonic acid, 2-hydroxyethyl (meth)acrylate, or styrene sulfonic acid, is copolymerized with acrylic acid within a range that does not deteriorate the performance of the superabsorbent polymer.

In the present invention, it is not essential for the absorbent member 30 to include the superabsorbent polymer 32. However, in cases where the absorbent member 30 includes the superabsorbent polymer 32, the ratio of the superabsorbent polymer 32 with respect to the weight of the absorbent member 30 is preferably from 5% to 95% by weight. In cases where the article is particularly a sanitary napkin or for absorbing a small amount of excreted fluid such as light incontinence, the ratio is preferably from 10% to 30% by weight. In cases where the article is for absorbing a large amount of excreted fluid, such as a disposable diaper, the ratio is preferably from 50% to 80% by weight.

From the standpoint of exhibiting stable absorbency, it is preferable that the amount of 0.9-percent-by-weight sodium chloride solution the absorbent core 10 can retain (i.e., the retention amount of the absorbent core 10) when fixed to the intermediate sheet 20 is equal to or above 0.1 g/g, and more preferably equal to or above 1 g/g, regardless of whether the absorbent members 30 include the superabsorbent polymer or not. In order to achieve such a retention amount, it is advantageous to use, in combination, a highly-hydrophilic fiber having a strong capillary force (such as pulp or rayon), a synthetic fiber that does not sink down even if wet (i.e., that is neither plasticized nor reduced in wet strength), and a superabsorbent polymer, as the material constituting the absorbent member 30.

The above-described retention amount is measured as follows. Measurement is carried out at 25±2° C. and at a relative humidity of 50% RH±5%. First, an evaluation sample is prepared by cutting out an intermediate sheet 20 with the absorbent members 30 fixed thereto into a square 50 mm long and 50 mm wide, and the weight ($M_0$) of the evaluation sample is measured. The evaluation sample is then placed in a 500 ml beaker containing 400 ml of a 0.9-percent-by-weight sodium chloride solution and immersed therein for one hour. After an hour, the evaluation sample is taken out from the beaker, and is placed on an acrylic plate inclined at 45 degrees and left thereon for ten minutes to drain. The weight ($M_1$) after draining is then measured. The retention amount is calculated from the following equation, and an average value for n=5 (i.e., an average value for five evaluation samples) is considered as the retention amount of the intermediate sheet 20, with the absorbent members 30 fixed thereto, with respect to the sodium chloride solution.

$$\text{Retention amount(g/g)} = (M_1 - M_0)/(M_0)$$

Materials having functions of drawing in and diffusing excreted fluid are used as the intermediate sheet 20 to which the absorbent members 30 are fixed. Examples of sheets having such functions include nonwoven fabrics, films, or porous elements including, for example, fibers having hydrophilic property or including fibers treated with a hydrophilic agent (hydrophilic oil solution) or the like. The sheet may be used as a single layer, or these sheets may constitute a multilayer structure in which a plurality of layers are laminated into a single sheet. From the standpoint of rendering the intermediate sheet a function of taking up the liquid component by means of capillary force, it is preferable to use nonwoven fabrics or porous elements. It is preferable that the basis weight of the intermediate sheet 20 is from 5 to 50 g/m$^2$, and more preferably from 10 to 30 g/m$^2$, regardless of whether the intermediate sheet 20 has a single-layer structure or a multilayer structure. Further, in order to achieve the function of diffusing excreted fluid, the absorption rate of physiological saline solution measured by D/W method of the intermediate sheet 20 is preferably equal to or above 0.05 ml/g·s, and more preferably from 0.05 to 0.5 ml/g·s, and even more preferably from 0.05 to 0.2 ml/g·s.

From the standpoint of absorbency and drawing property with respect to excreted fluid, it is preferable that the absorption rate of physiological saline solution measured by D/W method of each of the topsheet 101, the intermediate sheet 20, and the absorbent core 10 in the article 100 according to the present embodiment satisfies the following relationship: the topsheet 101<the intermediate sheet 20<the absorbent core 10. Such a relationship allows fluid to be transferred more deeply into the article 100 more easily when absorbing high-viscosity fluid. When absorbing low-viscosity fluid, it is preferable that the water-absorption rate of each of the intermediate sheet 20 and the topsheet 101 is lower than the rate for when absorbing high-viscosity fluid in order to provide superior strike-through. In order to arrange the absorption rate of each of the topsheet 101, the intermediate sheet 20, and the absorbent core 10 in the order described above, it is possible to use, for example, an air-through nonwoven fabric as the topsheet 101, a calendered air-through nonwoven fabric as the intermediate sheet 20, and pulp including superabsorbent polymer as the absorbent core 10.

The absorption rate of each component is as follows. The absorption rate of the absorbent core 10 is preferably from 0.1 to 5 ml/(g·s), and more preferably from 0.5 to 2 ml/(g·s). The preferred absorption rate of the intermediate sheet 20 is as described above: in case of absorbing high-viscosity fluid such as menstrual blood, the absorption rate is preferably from 0.05 to 0.5 ml/(g·s), and more preferably from 0.05 to 0.2 ml/(g·s); and in case of absorbing low-viscosity fluid such as urine, the absorption rate is preferably from 0.05 to 0.3 ml/(g·s), and more preferably from 0.05 to 0.1 ml/(g·s). The absorption rate of the topsheet 101 is preferably equal to or below 0.2 ml/(g·s), and more preferably from 0.01 to 0.2 ml/(g·s); in case of absorbing high-viscosity fluid, the absorption rate is preferably from 0.01 to 0.2 ml/(g·s), and more preferably from 0.01 to 0.1 ml/(g·s); and in case of absorbing low-viscosity fluid, the absorption rate is preferably equal to or below 0.1 ml/(g·s), and more preferably equal to or below 0.05 ml/(g·s). Note that the expression "absorption rate of a component" as used herein refers to an absorption rate of physiological saline solution determined according to the following measurement method, except where specifically noted.

The method for measuring the absorption rate of physiological saline solution (D/W method) is as follows. The device shown in FIG. 5($a$) is used for the measurement. This device includes a burette with a side cock. The burette has an inner diameter of 10.4 mm and a volume of 50 mL and is graduated. A rubber stopper (a silicone stopper is acceptable) is mounted to the top end opening of the burette so that the opening can be sealed. An end of a plastic tube having an inner diameter of 6 mm is connected to the bottom end of the burette. The other end of the plastic tube is connected to the bottom surface of a sample-holding platform. The sample-holding platform is shaped like a shallow Petri dish. There is an opening in the bottom surface of the sample-holding platform, and the other end of the plastic tube is connected to that opening. The sample-holding platform has an inner diameter of 53 mm and a depth of 6 mm. A glass filter (JIS G1; diameter: 52 mm Φ; thickness: 4.3 mm) is disposed in the sample-holding platform. A filter paper (No. 2; diameter: 70 mm) is placed on the glass filter.

Figure 5A:
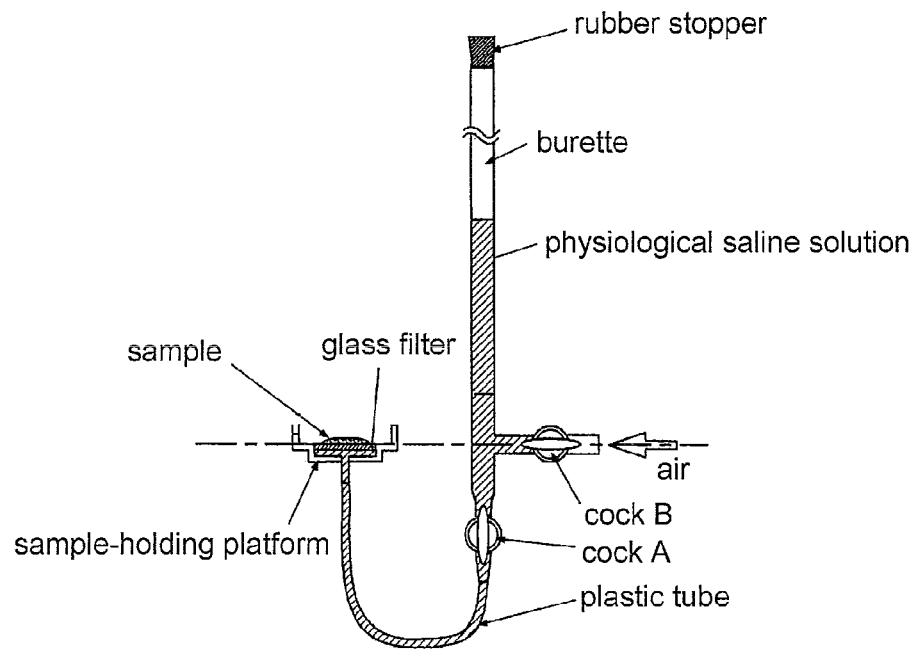
FIG. 5 is a diagram showing a device for measuring the absorption rate of physiological saline solution measured by D/W method.
Figure 5B:
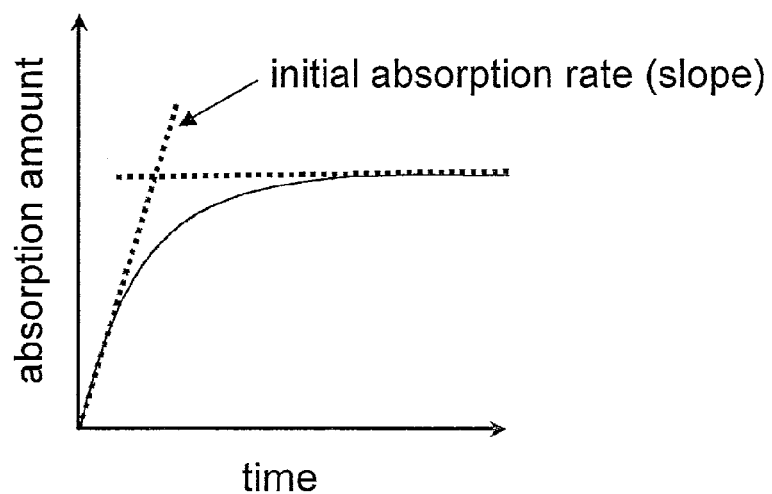

The procedure for measuring the absorption rate with the device shown in FIG. 5($a$) is as follows.

(1) Close cock B and open cock A. Pour a physiological saline solution into the burette, being careful not to leave any air in the plastic tube. The solution should be poured until the filter paper on the sample-holding platform becomes sufficiently wet.

(2) Close cock A and pour the physiological saline solution up to the calibration mark on the burette indicating 10 ml. Close the top end opening of the burette with the rubber stopper, and then open cock A.

(3) Open cock B and align the position of the upper surface of the filter paper on the sample-holding platform with the position of the central line of cock B, being careful so that no liquid settles in the conduit of cock B.

(4) Wipe off any excessive liquid on the filter paper. Align the liquid level of the burette to the calibration mark indicating 20 ml.

(5) Place a sample on the filter paper. At this time, the sample should be placed on the sample-holding platform so that the side of the sample to face the wearer's skin, when used in an absorbent article, comes in opposition to the filter paper.

(6) Start measuring time with a stopwatch when bubbles are released from cock B, and observe the change-over-time of the liquid level of the physiological saline solution in the burette for five minutes. The change in liquid level over time corresponds to the amount of physiological saline solution absorbed by the sample. The size of the sample may be changed arbitrarily in cases where the amount of bubbles released is small or the size of the released bubbles is small and it is difficult to perform measurement. FIG. 5($b$) shows the relationship between time and absorption amount as a graph; the relationship depicts a curve having a primary inflection point. A value obtained by dividing the slope up to the primary inflection point (i.e., the slope of the initial absorption rate) in this graph by the sample weight is defined as the "absorption rate".

Note that measurement of the absorption rate of the absorbent core 10 is performed in a state with the intermediate sheet 20 or the below-described base sheet 21 fixed on the fixing points 33. In this case, neither the intermediate sheet 20 nor the base sheet 21 come into contact with the filter paper surface, and the size of each fixing point 33 is relatively small. Therefore, no measurement error occurs even if measurement of the absorption rate of the absorbent core 10 is performed with the intermediate sheet 20 or the base sheet 21 fixed thereto. When measuring the absorption rate of the intermediate sheet 20 or the base sheet 21, the absorbent core 10 is removed with the fixing points 33 and all.

Figure 6:
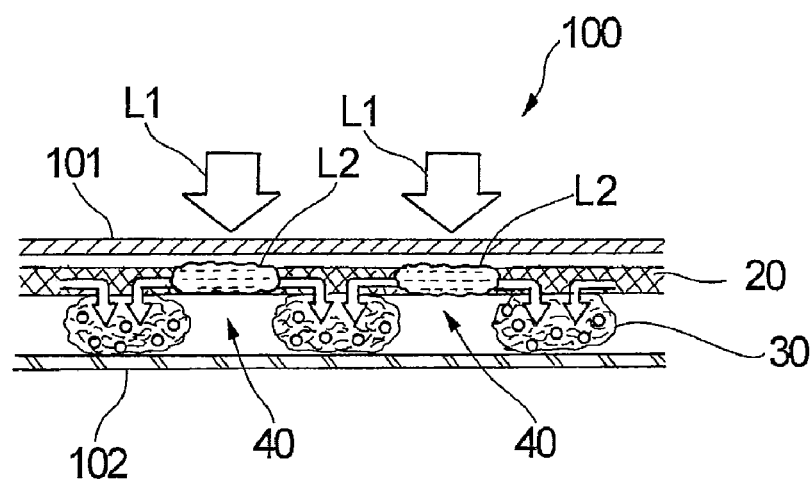
FIG. 6 is a schematic diagram showing how liquid is absorbed and retained in the absorbent article of FIG. 1.

FIG. 6 schematically shows how fluid is absorbed and retained in the absorbent article 100 of the present embodiment. The excreted fluid L1 first comes into contact with the topsheet 101. The fluid L1 is then quickly drawn into the intermediate sheet 20 that is in planar contact with the lower surface side of the topsheet 101 by the liquid-drawing function of the intermediate sheet 20. Thus, the surface of the topsheet 101 is always kept in a state providing superior dry feel.

The liquid L2 drawn into the intermediate sheet 20 is then diffused in the planar direction of the intermediate sheet 20 by the diffusing function thereof. The diffused liquid L2 is absorbed by the absorbent members 30 and thus transferred from the intermediate sheet 20 to the absorbent members 30. The fluid drawn into the absorbent members 30 is guided along spaces 40 that exist among the absorbent members 30 and is promptly diffused in the planar direction of the absorbent core 10. The spaces 40 in the absorbent core 10 according to the embodiment particularly shown in FIG. 2 are formed extending in both the length direction and the width direction of the absorbent article 100, and thus, the fluid is guided in every direction of the absorbent article 100. This isolates the fluid L2 from the topsheet 101, making it difficult for wet-back to occur.

As described above, the absorbent article of the present embodiment has a superior dry feel and is less prone to wet-back. In addition, forming the absorbent core 10 with the absorbent member group including a number of discretely-and-independently arranged absorbent members 30 improves the draping property of the article 100 owing to the spaces 40 existing among the absorbent members 30, and thus the article 100 becomes less prone to creases and kinks while worn. Further, in cases where the intermediate sheet 20 exhibits stretch property, fixing the absorbent members to such an intermediate sheet 20 allows the shape thereof to be easily restored against deformation such as bending.

Figure 7:
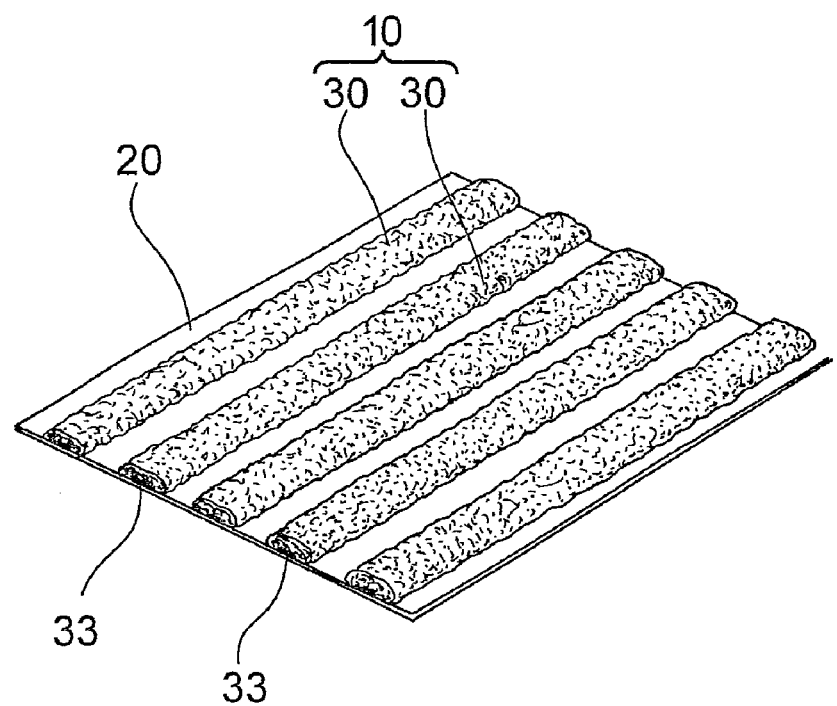
FIG. 7 is a perspective showing another embodiment of the absorbent members, which corresponds to FIG. 2.

FIG. 7 shows another embodiment of the absorbent core 10. In the absorbent core 10 of the embodiment shown in FIG. 7, each absorbent member 30 constitutes a belt-like element extending in one direction within the planar direction of the intermediate sheet 20, and the absorbent members 30 are arranged according to a pattern in which those belt-like elements are formed in a number of rows and parallel to one another. It is preferable to incorporate the absorbent core 10 of this embodiment into an absorbent article 100 in such a manner that the direction in which the absorbent members 30 are arranged matches either the length direction or the width direction of the absorbent article.

Figure 8A:
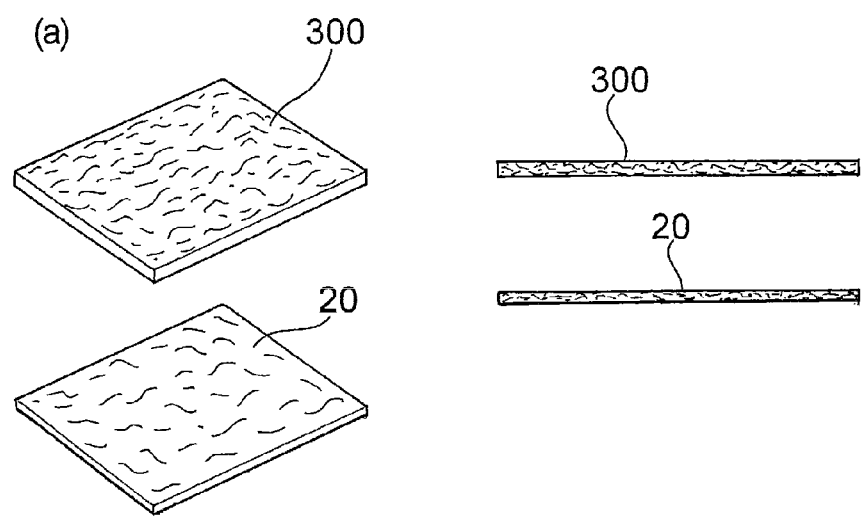
Figure 8B:
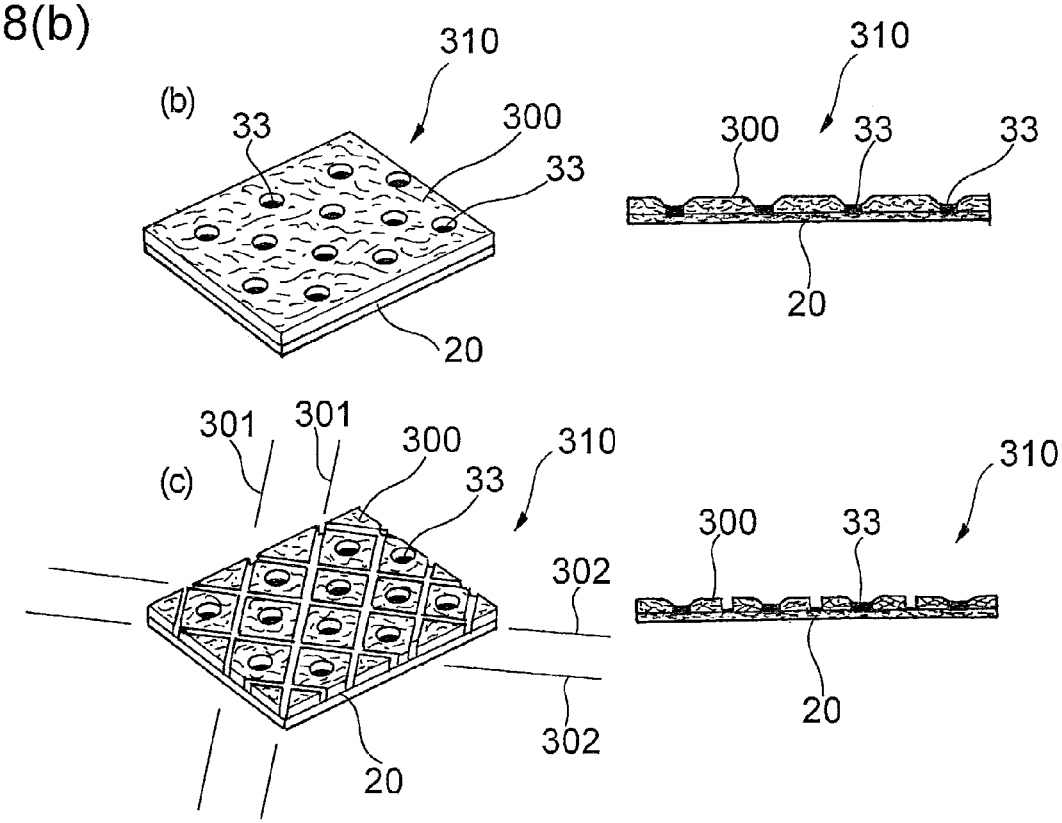

Now, a preferable process for producing the above-described absorbent core 10 is described with reference to FIGS. 8 to 11. In order to facilitate understanding of the process, FIG. 8 and FIG. 11 show the components in each production step using both perspectives and cross-sectional views. First, as shown in FIG. 8(*a*), an intermediate sheet 20 and a fibrous sheet 300 are prepared. A sheet of the above-described type is used as the intermediate sheet 20. A heat-shrinkable sheet including a heat-shrinkable fiber is used as the fibrous sheet 300. It is preferable that the heat-shrinkable fiber is a heat-crimping fiber. The fibrous sheet 300 may further include, as necessary, rayon, synthetic fibers that are not heat shrinkable, and/or water-absorbent fibers. A fibrous web may be used as the fibrous sheet 300. A "fibrous web" is an aggregation of fiber in which the constituent fibers are entangled together loosely to such a degree that the fibers cannot be kept in a sheet-like structure. In cases where high stability is required for carrying the fibrous sheet 300, a nonwoven fabric may be used as the fibrous sheet 300 instead of a fibrous web. When using a nonwoven fabric, it is preferable to use one that is made using non-thermal means, such as ultrasonic embossing, binders, or needle-punching, in order to keep the heat-shrinkable fiber from shrinking during the step of producing the nonwoven fabric. It is, however, possible to use a nonwoven fabric made using thermal means, such as the air-through process, as long as the obtained nonwoven fabric exhibits heat shrinkability.

After the fibrous sheet 300 is superposed on one side of the intermediate sheet 20, the sheets are partially joined together to form a plurality of fixing points 33 as shown in FIG. 8(*b*), thereby obtaining a laminate 310. In forming the fixing points 33, it is preferable to use non-thermal means, such as ultrasonic embossing or an adhesive such as a hot melt adhesive. It is, however, possible to use thermal means, such as hot embossing, as long as the fibrous sheet 300 having the fixing points 33 formed thereon exhibits heat shrinkability.

Figure 9:
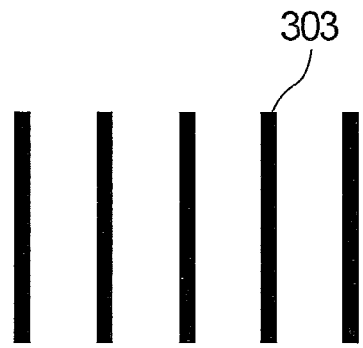
FIG. 9 is a diagram showing a pattern according to which fibers constituting a fibrous sheet in a laminate are cut.

Then, superabsorbent polymer is sprinkled onto the fibrous sheet 300 as necessary (not shown). Thereafter, the fibers constituting the fibrous sheet 300 are cut between adjacent fixing points 33, as shown in FIG. 8(*c*). Here, it is important that only the fibers constituting the fibrous sheet 300 are cut, and not the intermediate sheet 20. In the present embodiment, only the fibers constituting the fibrous sheet 300 are cut along a number of first cut lines 301 extending in a straight line and parallel to one another and a number of second cut lines 302 intersecting with the first cut lines 301 and extending in a straight line and parallel to one another. The cutting pattern, however, is not limited to the above, and for example, the fibrous sheet may be cut in such a manner that the cut sections 303 extend in a number of straight lines parallel to one another, as shown in FIG. 9. Cutting the fibers constituting the fibrous sheet 300 according to the pattern shown in FIG. 9 allows the previously-described absorbent core 10 shown in FIG. 7 to be produced. Note that, in place of the straight-line cutting pattern shown in FIG. 9, it is possible to adopt various cutting patterns, such as smooth wavy lines shaped like a sinusoidal wave or angled wavy lines.

Figure 10A:
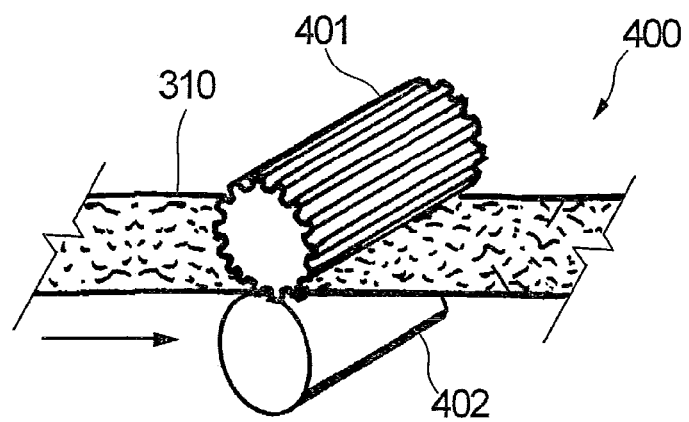
FIG. 10(a) is a schematic diagram showing a device for cutting the fibers constituting the fibrous sheet in the laminate.
Figure 10B:
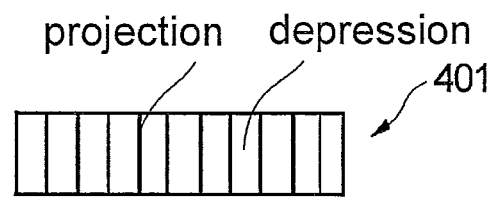
FIGS. 10(b) and 10(c) are schematic diagrams respectively showing different shapes of a first roller in the device shown in FIG. 10(a).
Figure 10C:
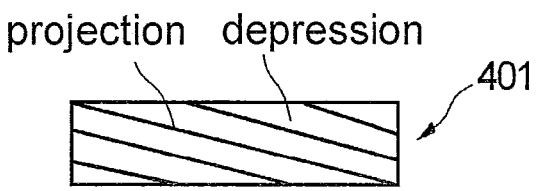

In order to cut the fibers constituting the fibrous sheet 300 of the laminate 310, it is possible, for example, to use a cutting device 400 including a first roller 401 and a second roller 402 as shown in FIG. 10(*a*). The first roller 401 that is used is a pattern-indented roller (roller with grooved blades) in which axially-extending depressions (blades) and projections (grooves) are alternately arranged along the rotating direction of the roller. The tip end of each projection forms a sharp cutting blade. The second roller 402 is a metal or rubber roller having a smooth surface. The laminate 310 is passed between the rollers in such a manner that the fibrous sheet 300 of the laminate 310 is faced toward the first roller 401, and in this way, only the fibers constituting the fibrous sheet 300 of the laminate 310 are cut. The cut lines 301 and 302 of the pattern shown in FIG. 8(*c*) can be formed by passing the laminate 310 between the rollers 401 and 402 at least twice while changing the angle at which the laminate 310 is passed between the rollers 401 and 402 every time the laminate is passed. Note that the fibrous sheet 300 may be cut according to various patterns by using, alone or in combination, rollers having such patterns as those shown in FIGS. 10(*b*) and 10(*c*) as the first roller 401.

Figure 11A:
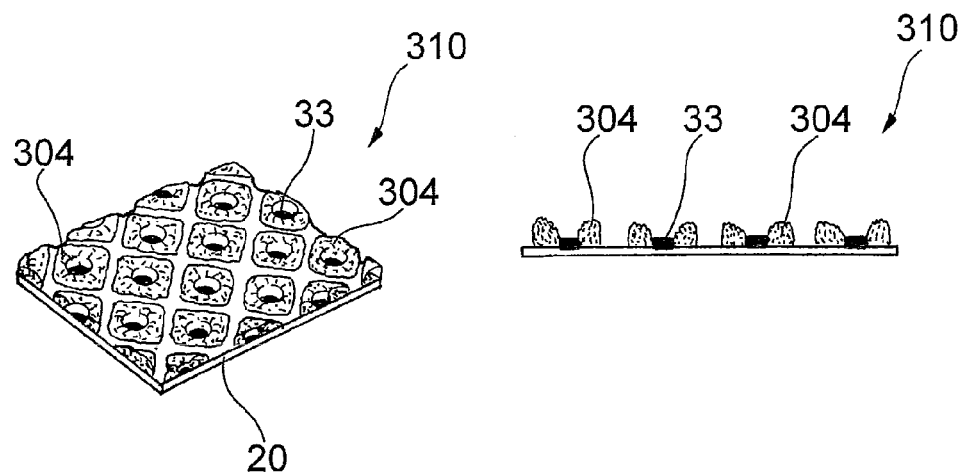
FIGS. 11(a) and 11(b) are process flow diagrams sequentially showing a process for producing the absorbent members of FIG. 2 following the step of FIG. 8(c).

After cutting the fibers constituting the fibrous sheet 300, heat is applied to the laminate 310 to cause the heat-shrinkable fiber contained in the fibrous sheet 300 to shrink. The temperature of the applied heat is set equal to or above the shrink-start temperature of the heat-shrinkable fiber and below the melt temperature. Through heat shrinking, the fibers constituting the fibrous sheet 300 gather toward each fixing point 33 as well as rise up in the thickness direction as shown in FIG. 11(a), thereby forming annular raised sections 304. Each annular raised section 304 is located around a fixing point 33 so as to surround that fixing point 33. Controlling the extent to which the heat-shrinkable fiber is shrunk allows the distance between adjacent absorbent members 30 in the intended absorbent core 10 to take a desired value.

Figure 11B:
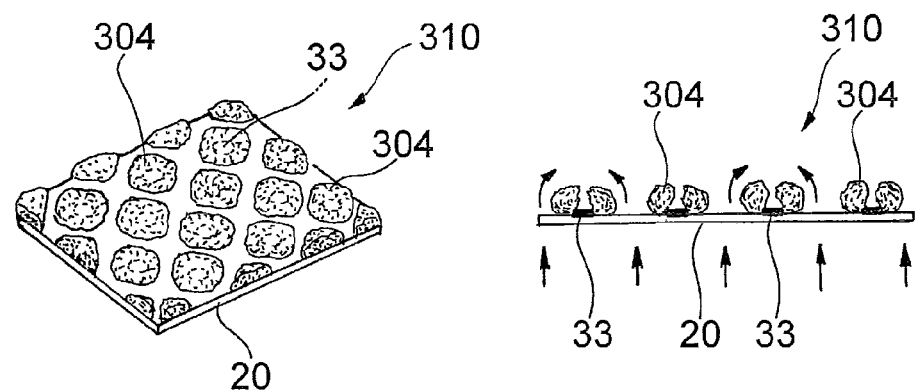

Then, as shown in FIG. 11(b), air is blown from the side of the intermediate sheet 20 in the laminate 310. The blown air passes through the intermediate sheet 20 and uplifts the fibers constituting the annular raised sections 304 around the respective fixing points 33. With this uplift, the fibers constituting the annular raised sections 304 thermally shrink and gather onto the respective fixing points 33, thus forming domical raised sections on the respective fixing points 33. These raised sections constitute the absorbent members 30 in the intended absorbent core 10. In this way, the intended absorbent core 10 is made. Further, by blowing air as shown in FIG. 11(b) while causing the heat shrinking shown in FIG. 11(a), the heat-shrinkable fiber is entangled with the fibers constituting the fibrous sheet 300 while shrinking, and in this way, the raised sections are successively formed on the respective fixing points 33.

Note that the operation shown in FIG. 11(b) is effective in cases where the intermediate sheet 20 has sufficient breathability. In cases where the intermediate sheet 20 has no breathability or extremely poor breathability, it is preferable to blow air in the transverse direction (horizontal direction) onto the fibers constituting the fibrous sheet 300 or the annular raised sections 304, in place of the operation shown in FIG. 11(b). In that case, a single raised section can successively be formed on each fixing point 33 by blowing air in two orthogonal directions.

In the present invention, it is also possible to use an intermediate product in the process of producing the absorbent members 30 shown in FIG. 2—i.e., the intermediate product in the state shown in FIG. 11(a)—as another embodiment of the absorbent members. In the absorbent members comprising the intermediate product shown in FIG. 11(a), each absorbent member has an annular raised section located around a fixing point so as to surround that fixing point, as shown in the figure.

Next, second to eighth embodiments of the present invention are described with reference to FIGS. 12 to 22. As for these second to eighth embodiments, the detailed explanation on the first embodiment applies as appropriate to the features that are not particularly described in the following. Further, in FIGS. 12 to 22, the same components as those in FIGS. 1 to 11 are accompanied with the same reference numerals.

Figure 12:
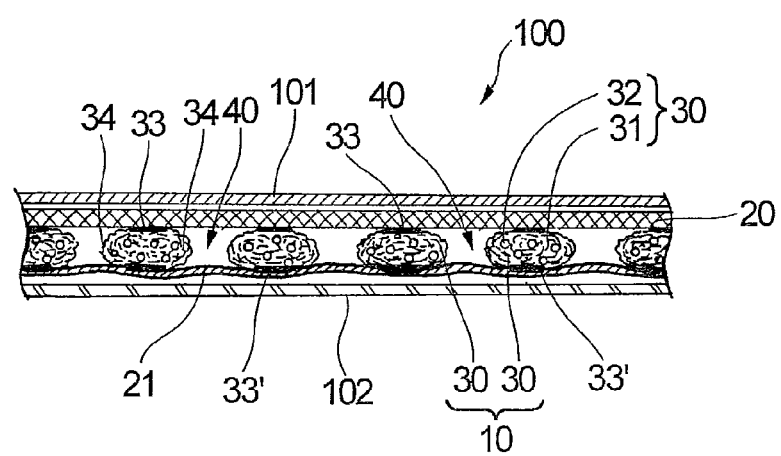
FIG. 12 is a schematic diagram (corresponding to FIG. 1) showing a cross-sectional structure of an absorbent article according to a second embodiment of the present invention taken along the width direction in the lengthwise middle region of the absorbent article.

In the second embodiment shown in FIG. 12, an absorbent core 10 which has the absorbent member group including the absorbent members 30 is disposed between a topsheet 101 and a backsheet 102. An intermediate sheet 20 is disposed between the absorbent core 10 and the topsheet 101. Further, a base sheet 21 is disposed between the absorbent core 10 and the backsheet 102. The absorbent members 30 are fixed to the lower surface of the intermediate sheet 20 through respective fixing points 33. The absorbent members 30 are also fixed to the upper surface of the base sheet 21 through respective fixing points 33'. In this embodiment, the absorbent members 30 are fixed to the base sheet 21 in the same manner as the absorbent members 30 are fixed to the intermediate sheet 20. The side of the base sheet 21 without the absorbent members 30 may be joined to the backsheet 102, but does not necessarily have to be joined thereto.

A sheet material to which the absorbent members 30 can be fixed is used as the base sheet 21 of the present embodiment. For example, it is possible to use, as the base sheet 21, a material similar to that of the intermediate sheet 20—i.e., a material having functions of drawing in and diffusing liquid.

The base sheet 21 may or may not be permeable to liquid. The property of the base sheet 21 regarding liquid permeability can be selected as appropriate depending on the intended use of the absorbent article 100. The liquid permeability of the base sheet 21 is determined, for example, according to the type of constituent material used and how the base sheet 21 is produced.

Further, the base sheet 21 may or may not have stretch property. In cases where the base sheet 21 has stretch property, the base sheet 21 has stretch property in at least one direction within its plane. In cases where the base sheet 21 has stretch property, the base sheet 21 serves as a part for rendering the absorbent core 10 stretchable. The term "stretchable (stretch property)" refers to a property that allows an element to be extended and to be contracted by canceling the extended state. The direction in which the base sheet 21 extends and contracts within a plane depends, for example, on how the base sheet 21 is produced. Preferably, the base sheet 21 is stretchable in two directions—i.e., a certain direction within a plane and a direction orthogonal thereto—, and more preferably, stretchable in all directions within a plane.

In cases where the base sheet 21 has stretch property, it is preferable that the intermediate sheet 20 also has stretch property. In this case, it is preferable that the absorbent members 30 are fixed to the base sheet 21 through respective fixing points 33' and fixed to the intermediate sheet 20 through respective fixing points 33 in such a design that the shape of each of the absorbent members 30 is not deformed upon stretch of the base sheet 21 and the intermediate sheet 20. In order to keep the shape of each absorbent member 30 from deforming upon stretch of the base sheet 21 and the intermediate sheet 20, it is advantageous that the base sheet 21 does not exhibit stretch property at the fixing points 33' and the intermediate sheet 20 does not exhibit stretch property at the fixing points 33. Due to the fixing points 33 and 33' not exhibiting stretch property, the base sheet 21 and the intermediate sheet 20 do not stretch at the fixing points 33 and 33', even when the base sheet 21 and the intermediate sheet 20 as a whole are stretched. Thus, the absorbent members 30 fixed to the base sheet 21 and the intermediate sheet 20 respectively through the fixing points 33 and 33' are not influenced by the stretch of the base sheet 21 and the intermediate sheet 20, which keeps the shape of each absorbent member from deforming upon stretch of the base sheet 21 and the intermediate sheet 20. Because the absorbent members 30 do not deform in shape, the absorbency hardly changes even upon stretch of the base sheet 21 and the intermediate sheet 20. Therefore, the absorbent article 100 exhibits stable absorbency throughout the period worn.

In order to keep the base sheet 21 and the intermediate sheet 20 from exhibiting stretch property at the fixing points 33 and 33', the stretch property of the base sheet 21 and the intermediate sheet 20 may be eliminated, for example, by forming the fixing points 33 and 33' through ultrasonic embossing. Forming the fixing points 33 and 33' with an adhesive such as a hot melt adhesive also allows the stretch property of the base sheet 21 and the intermediate sheet 20 to be eliminated.

Figure 13A:
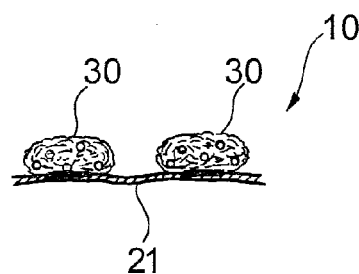
FIG. 13 is a schematic diagram showing states of the absorbent members when a base sheet of the absorbent article of FIG. 12 is contracted and stretched.
Figure 13B:
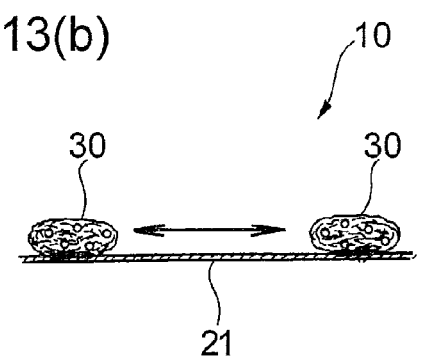

In cases where the base sheet 21 and the intermediate sheet 20 have stretch property, it is preferable that the fixing points 33 and 33' do not exhibit stretch property, as described above. In other words, it is preferable that only sections between the fixing points 33 and 33' exhibit stretch property in the base sheet 21 and the intermediate sheet 20. That is, when the base sheet 21 in its natural state (relaxed state) as shown in FIG. 13(*a*) is extended in its planar direction, only the sections between the fixing points 33' extend as shown in FIG. 13(*b*). Here, the absorbent members 30 do not deform in shape. When the extended state of the base sheet 21, which is in its extended state as shown in FIG. 13(*b*), is canceled, only the sections between the fixing points 33' contract, causing no deformation in the shape of the absorbent members 30. Since the base sheet 21 has such a stretch property, the absorbent core 10 is superior in adaptability to a wearer's body and conformability to a wearer's movement. Note that the extended and contracted states of the intermediate sheet 20 are omitted from FIGS. 13(*a*) and 13(*b*) for convenience' sake.

As described previously, a sheet-like material with or without stretch property is used as the base sheet 21 to which the absorbent members 30 are fixed. In cases where the base sheet 21 does not have stretch property, it is possible to use, for example, ordinary nonwoven fabrics or ordinary films with or without perforation as the base sheet 21. In cases where the base sheet 21 has stretch property, any kind of sheet having stretch property can be used as the base sheet 21, without particular limitation. Examples of such sheets may include nonwoven fabrics that include, as a constituent, fiber including elastic resin (i.e., elastic nonwoven fabrics), and films including elastic as resin (i.e., elastic films). Any type of elastic nonwoven fabric or elastic film known in the present technical field can be used. It is preferable that the basis weight of the base sheet 21 is from 5 to 50 g/m$^2$, and more preferably from 10 to 30 g/m$^2$, regardless of whether the base sheet 21 has or does not have stretch property.

It is preferable that the degree of stretch property of the base sheet 21 is 60% or above, and more preferably 80% or above, in stretch ratio which is measured as follows, from the standpoint of providing particularly favorable adaptability to a wearer's body and conformability to a wearer's movement. The stretch ratio is measured as follows. Measurement is carried out using a tension/compression tester RTC-1210A (supplied by Orientec Co., Ltd.) in the "tension mode". First, a measurement piece is sampled by cutting the base sheet 21 into a strip 25 mm wide and 150 mm long. The measurement piece is set between air chucks that are installed in the tension/compression tester at an initial sample length (chuck-to-chuck distance) of 100 mm, and the piece is extended by raising the chuck mounted to the load cell (rated output of 5 kg) of the tension/compression tester at a speed of 300 mm/min. When the measurement piece has been extended by a length 50% of the initial sample length, i.e., by 50 mm, the movement direction of the chuck is reversed, and the chuck is lowered at a speed of 300 mm/min and returned to the position of the initial sample length. During this operation, the relationship between the load detected by the load cell and the extension of the measurement piece is recorded in a chart, and the stretch ratio is obtained from the following equation (1) based on the chart.

$$\text{Stretch ratio} = \text{Recovery extension}/\text{Maximum extension length}(=50 \text{ mm}) \tag{1}$$

The "recovery extension" is defined as the distance the chuck has moved from the maximum extension length (=50 mm) at the time the load first becomes zero after starting to lower the chuck from the maximum extension length. Note that in cases where the measurement piece cannot extend up to the above-described size, measurement is carried out according to the following method.

<Test Piece>

Assuming that the length of the sheet in the chuck-to-chuck direction is L mm, the length of a section that is held is S mm, and the width of the sheet is C mm, a measurement piece is sampled by cutting the base sheet into a test piece (L+2S) mm long×C mm wide in such a manner that the length ratio L:C becomes 3:5.

<Test>

The test piece is set to the tension/compression tester at a chuck-to-chuck distance of L, and the chuck is raised at a speed of 100×(L/30) mm/min until the measurement piece is extended by a length 50% of the initial sample length. The movement direction of the chuck is then reversed, and the chuck is lowered at a speed of 100×(L/30) mm/min and returned to the position of the initial sample length. Calculation is made according to the following equation (2):

$$\text{Stretch ratio} = \text{Recovery extension}/\text{Maximum extension length}(=L/2 \text{ mm}) \tag{2}$$

In cases where the base sheet 21 has stretch property, it is preferable that the topsheet 101 and the backsheet 102 of the absorbent article 100 also have stretch property. Further, as described above, it is preferable that the intermediate sheet 20 also has stretch property. In this way, the entire absorbent article 100 is provided with stretch property as a whole. As a topsheet 101 having stretch property, it is possible to use, for example, a nonwoven fabric that includes, as its constituent, fibers including elastic resin, or a perforated film including elastic resin. Such nonwoven fabrics and films have liquid permeability. As a backsheet 102 having stretch property, it is possible to use a film including elastic resin, the film being impermeable or hardly permeable to liquid. The film may be moisture permeable. As an intermediate sheet 20 having stretch property, it is possible to use, for example, nonwoven fabrics that include, as a constituent, fiber including elastic resin (i.e., elastic nonwoven fabrics), or elastic porous elements made of elastic resin having a structure formed into a three-dimensional network by means of foaming etc.

Figure 14:
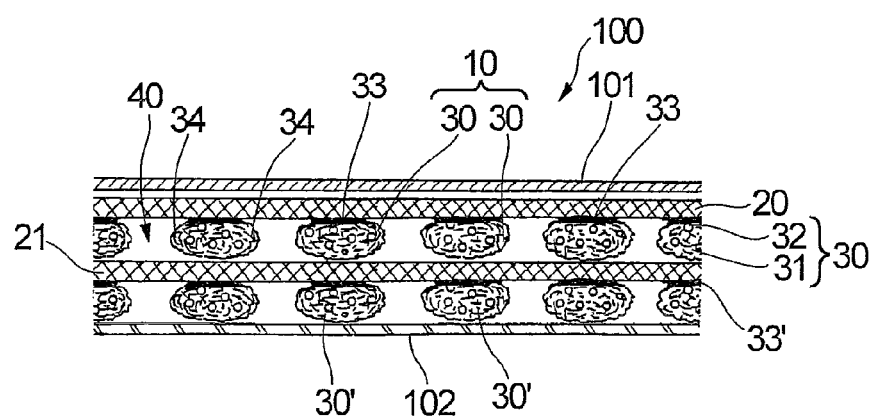
FIG. 14 is a schematic diagram (corresponding to FIG. 1) showing a cross-sectional structure of an absorbent article according to a third embodiment of the present invention taken along the width direction in the lengthwise middle region of the absorbent article.

In the third embodiment shown in FIG. 14, an absorbent core 10 having a number of absorbent members 30 is disposed between a topsheet 101 and a backsheet 102. An intermediate sheet 20 is disposed between the absorbent core 10 and the topsheet 101. The lower surface of the intermediate sheet 20 and the upper surface of each absorbent member 30 are fixed together through a fixing point 33 in such a manner that the absorbent member 30 has an overhang 34 formed thereon. Further, a liquid-permeable base sheet 21 is disposed between the absorbent core 10 and the backsheet 102. A number of discretely and independently arranged second absorbent members 30' are located across the planar direction of the article 100 between the base sheet 21 and the backsheet 102. The second absorbent members 30' may be arranged according to the pattern shown in FIG. 2 or the pattern shown in FIG. 7. The upper surface of each second absorbent member 30' is fixed to the lower surface side of the base sheet 21 through a fixing point 33'. The second absorbent members 30' are fixed to the base sheet 21 in the same manner as the absorbent members 30 are fixed to the intermediate sheet 20. Further, the explanation on the absorbent members 30 applies as appropriate to the constituent material, shape, size, etc., of the second absorbent members 30'. Furthermore, the explanation on the second embodiment applies as appropriate to the base sheet 21, on the condition that the base sheet 21 is permeable to liquid. The lower surface side of the absorbent members 30 is not fixed to the upper surface side of the base sheet 21. Likewise, the lower surface side of the second absorbent members 30' is not fixed to the upper surface side of the backsheet 102. The present embodiment is advantageous in that the liquid-absorption capacity can be increased. Also, absorbing and retaining the excreted fluid with the second absorbent members 30' isolates the fluid from the topsheet 101, thereby further improving the dry feel of the topsheet 101 as well as making it even more difficult for wet-back to occur.

Figure 15:
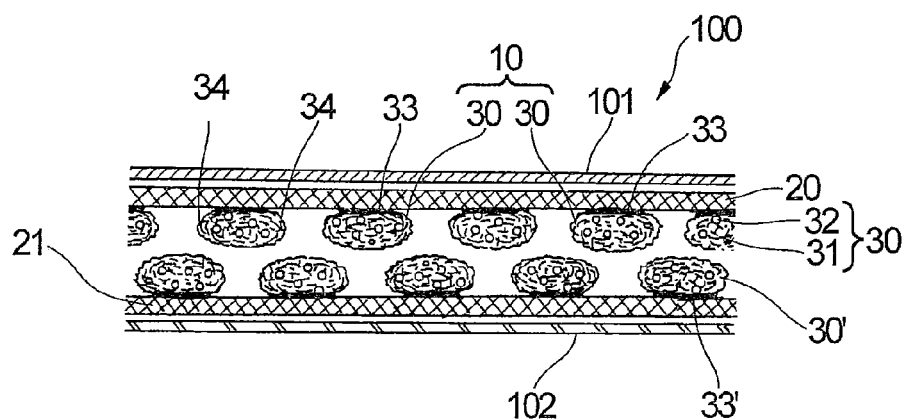
FIG. 15 is a schematic diagram (corresponding to FIG. 1) showing a cross-sectional structure of an absorbent article according to a fourth embodiment of the present invention taken along the width direction in the lengthwise middle region of the absorbent article.

In the fourth embodiment shown in FIG. 15, an absorbent core 10 having a number of absorbent members 30 is disposed between a topsheet 101 and a backsheet 102. An intermediate sheet 20 is disposed between the absorbent core 10 and the topsheet 101. The lower surface of the intermediate sheet 20 and the upper surface of each absorbent member 30 are fixed together through a fixing point 33 in such a manner that the absorbent member 30 has an overhang 34 formed thereon. Further, a base sheet 21 is disposed between the intermediate sheet 20 and the backsheet 102. A number of discretely and independently arranged second absorbent members 30' are located across the planar direction of the article 100 between the base sheet 21 and the intermediate sheet 20, and are disposed in a non-opposing state with respect to the absorbent members 30. That is, the absorbent members 30 and the second absorbent members 30' are arranged in a mutually-nesting state. The term "non-opposing state" refers to a state in which the absorbent members 30 and the second absorbent members 30' are not completely in the same position when viewing the absorbent article 100 from above. (Hereinafter, the term "non-opposing state" is used in this meaning.) Accordingly, a state in which the absorbent members 30 and the second absorbent members 30' are arranged in a partially-overlapped state when viewing the absorbent article 100 from above is encompassed within the term "non-opposing state". Therefore, in cases where the absorbent members 30 are arranged according to the pattern shown in FIG. 2, the second absorbent members 30' will also be arranged according to the pattern shown in the same figure. Likewise, in cases where the absorbent members 30 are arranged according to the pattern shown in FIG. 7, the second absorbent members 30' will also be arranged according to the pattern shown in the same figure. The lower surface of each second absorbent member 30' is fixed to the upper surface side of the base sheet 21 through a fixing point 33'. The second absorbent members 30' are fixed to the base sheet 21 in the same manner as the absorbent members 30 are fixed to the intermediate sheet 20. Further, the explanation on the absorbent members 30 applies as appropriate to the constituent material, shape, size, etc., of the second absorbent members 30'. Furthermore, the explanation on the second embodiment applies as appropriate to the base sheet 21. The base sheet 21 may or may not have liquid permeability. The lower surface side of the absorbent members 30 is not fixed to the upper surface side of the base sheet 21. Likewise, the upper surface side of the second absorbent members 30' is not fixed to the lower surface side of the intermediate sheet 20. The present embodiment is advantageous in that the liquid diffusibility in the planar direction of the article 100 is further improved. This advantage becomes even more significant in cases where the same type of sheet as the intermediate sheet 20 is used as the base sheet 21.

The embodiments described above are examples in which the intermediate sheet 20 is disposed between the topsheet 101 and the absorbent core 10. The following embodiments are examples in which the intermediate sheet 20 is disposed between the backsheet 102 and the absorbent core 10.

Figure 16:
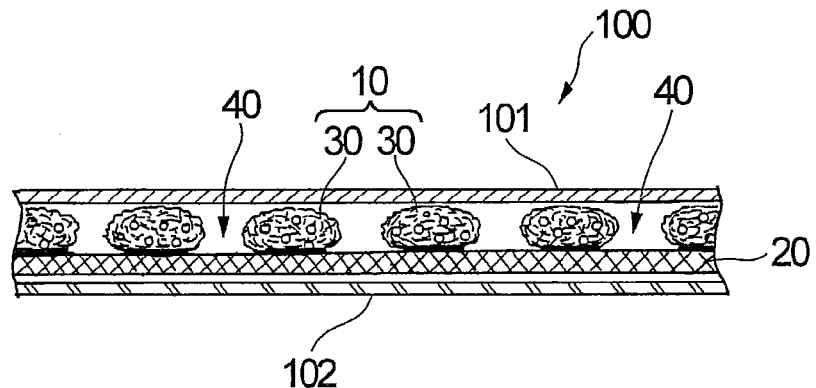
FIG. 16 is a schematic diagram showing a cross-sectional structure of a fifth embodiment of an absorbent article of the present invention taken along the width direction in the lengthwise middle region of the absorbent article.

In an article 100 according to the fifth embodiment shown in FIG. 16, an intermediate sheet 20 is disposed between an absorbent core 10 and a backsheet 102. The upper surface of each absorbent member 30 in the absorbent core 10 may be fixed to the lower surface of the topsheet 101, but does not necessarily have to be fixed thereto. In either case, the upper surface of each absorbent member 30 is in contact with the lower surface of the topsheet 101.

The overhang 34 (see FIG. 4 described previously) in each absorbent member 30 may be spaced from the intermediate sheet 20, or the bottom surface of the overhang 34 may be in contact with the upper surface of the intermediate sheet 20. In either case, however, the absorbent member 30 is not fixed to the intermediate sheet 20 at its overhang 34. Providing an overhang 34 to each absorbent member 30 gives the absorbent core 10 the advantage of maintaining a superior draping property by minimizing an increase in the total area of the fixing points 33 which causes deterioration in the draping property of the intermediate sheet 20, while allowing the absorbency of the absorbent members 30, and thus the property of preventing wet-back, to be improved by increasing the total area of the absorbent members 30.

From the standpoint of providing sufficient strength so that the absorbent member 30 does not fall off from the intermediate sheet 20 due to deformation caused by the wearer's movement etc., it is preferable that the area of each fixing point 33 (see FIG. 4 described previously) for fixing the absorbent member 30 to the intermediate sheet 20 is from 1 to 100 mm$^2$, and more preferably from 5 to 50 mm$^2$, provided that the area of the fixing point is smaller than that of the absorbent member 30 when viewed from above. Furthermore, from the standpoint of improving retainability of high-viscosity fluid retained among the absorbent members as well as maintaining the draping property of the intermediate sheet 20, it is preferable that the total sum of the area of the fixing points 33, as viewed from above, is from 5% to 95%, and more preferably from 20% to 70%, with respect to the area of the intermediate sheet 20.

From the standpoint of absorbency and drawing property with respect to excreted fluid, it is preferable that, in the article 100 according to the present embodiment, the absorption rate of physiological saline solution measured by D/W method of the intermediate sheet 20 and the absorption rate of the absorbent core 10 are higher than the absorption rate of the topsheet 101. Further, it is preferable that the absorption rate of each of the topsheet 101, the intermediate sheet 20, and the absorbent core 10 satisfies the following relationship: the topsheet 101<the intermediate sheet 20<the absorbent core 10. When absorbing high-viscosity fluid such as soft feces, such a relationship allows the fluid to pass through the topsheet 101 easily to thus provide superior strike-through, and also allows the fluid to be transferred easily to the absorbent members 30 or to the spaces among the absorbent members 30. Further, the fluid drawn into the intermediate sheet 20 from the spaces among the absorbent members 30 can easily be transferred into the absorbent members 30 by providing the absorption rate of physiological saline solution measured by D/W method in the following order: the topsheet 101<the intermediate sheet 20<the absorbent core 10. When absorbing low-viscosity fluid, it is preferable that the water-absorption rate of each of the intermediate sheet 20 and the topsheet 101 is lower than the rate for when absorbing high-viscosity fluid in order to provide superior strike-through. In order to provide the absorption rate of each of the intermediate sheet 20 and the absorbent core 10 in the order described above, it is possible to use, for example, an air-through nonwoven fabric as the topsheet 101, a calendered air-through nonwoven fabric as the intermediate sheet 20, and pulp including superabsorbent polymer as the absorbent core 10.

Figure 17:
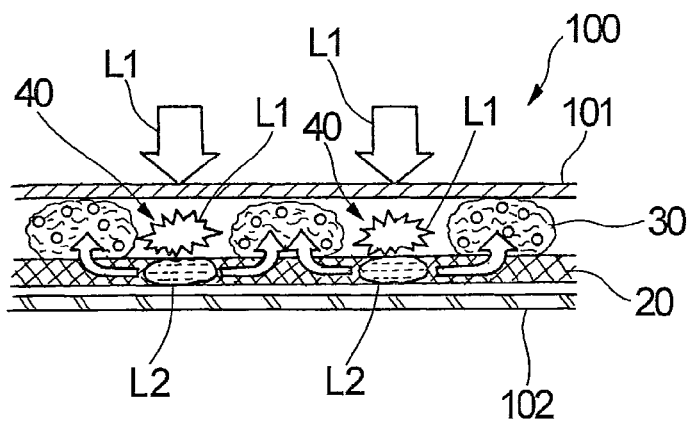
FIG. 17 is a schematic diagram showing how liquid is absorbed and retained in the absorbent article of FIG. 16.

FIG. 17 schematically shows how high-viscosity fluid is absorbed and retained in the article 100 of the present embodiment. High-viscosity fluid L1 such as excreted soft feces first comes into contact with the topsheet 101 having satisfactory liquid permeability. By permeating through the topsheet 101 or passing through the absorbent members 30, the high-viscosity fluid L1 is then retained by the absorbent members 30 as well as in the spaces 40 formed among the absorbent members 30. The liquid component L2 in the high-viscosity fluid L1 retained in the spaces is drawn into the intermediate sheet 20 due to the liquid-drawing function thereof. Further, the liquid component L2 drawn into the intermediate sheet 20 is transferred through the fixing points 33 and to the absorbent members 30 fixed on the upper surface side of the intermediate sheet 20, and is retained by the absorbent members 30. Thus, soft feces can be dried easily, which makes it difficult for wet-back to occur.

The liquid component L2 in the high-viscosity fluid drawn into the intermediate sheet 20 is diffused in the planar direction of the intermediate sheet 20 due to the diffusing function thereof. The diffused liquid component L2 is absorbed by the absorbent members 30 and thus transferred from the intermediate sheet 20 to the absorbent members 30. This allows the high-viscosity fluid L1 to be stably retained in the absorbent core 10. To achieve such functions easily, it is preferable to adopt, for the absorbent core, a structure having a stronger capillary force than the intermediate sheet—i.e., a structure that is highly hydrophilic and/or that has finer liquid-drawing spaces.

As described above, the absorbent article 100 of the present embodiment allows soft feces to dry easily and improves retainability of soft feces. In addition, forming the absorbent core 10 with a group of absorbent member including a number of discretely-and-independently arranged absorbent members 30 improves the draping property of the article 100 owing to the spaces 40 existing among the absorbent members 30, and thus the article 100 becomes less prone to creases and kinks while worn. Further, in cases where the intermediate sheet 20 exhibits stretch property, fixing the absorbent members to such an intermediate sheet 20 allows the shape thereof to be easily restored against deformation such as bending.

Figure 18:
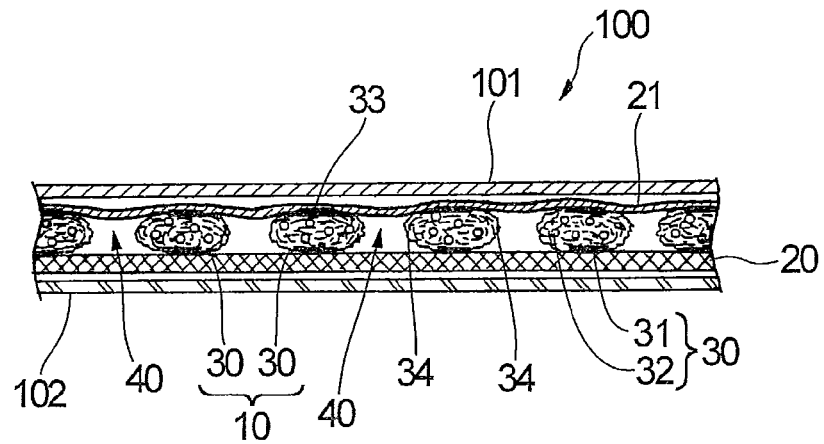
FIG. 18 is a schematic diagram (corresponding to FIG. 16) showing a cross-sectional structure of an absorbent article according to a sixth embodiment of the present invention taken along the width direction in the lengthwise middle region of the absorbent article.

In the sixth embodiment shown in FIG. 18, an absorbent core 10 having a group of absorbent member including a number of absorbent members 30 is disposed between the topsheet 101 and the backsheet 102. An intermediate sheet 20 is disposed between the absorbent core 10 and the backsheet 102. Further, a base sheet 21 is disposed between the absorbent core 10 and the topsheet 101. The absorbent members 30 are fixed to the lower surface of the base sheet 21 through respective fixing points 33. The absorbent members 30 are also fixed to the upper surface of the intermediate sheet 20. In the present embodiment, the absorbent members 30 are fixed to the base sheet 21 in the same manner as the absorbent members 30 are fixed to the intermediate sheet 20 in the fifth embodiment. The side of the base sheet 21 without the absorbent members 30 may be joined to the topsheet 101, but does not necessarily have to be joined thereto.

The same kinds of sheets as those used in the second embodiment described previously can be used as the base sheet 21, without particular limitation. The base sheet 21 used in the present embodiment, however, has liquid permeability.

The absorbent members 30 are fixed to the lower surface of the base sheet 21. In cases where the base sheet 21 has stretch property, it is preferable that the intermediate sheet 20 also has stretch property. In this case, it is preferable that the absorbent members 30 are fixed to the base sheet 21 through respective fixing points 33 in such a design that the shape of each of the absorbent members 30 is not deformed upon stretch of the base sheet 21 and the intermediate sheet 20. In order to keep the shape of each absorbent member 30 from deforming upon stretch of the base sheet 21, it is advantageous that the base sheet 21 does not exhibit stretch property at the fixing points 33. Due to the fixing points 33 not exhibiting stretch property, the base sheet 21 does not stretch at the fixing points 33, even when the base sheet 21 is stretched. Thus, the absorbent members 30 fixed to the base sheet 21 respectively through the fixing points 33 are not influenced by the stretch of the base sheet 21, which keeps the shape of each absorbent member from deforming upon stretch of the base sheet 21. Because the absorbent members 30 do not deform in shape, the absorbency hardly changes even upon stretch of the base sheet 21. Therefore, the absorbent article 100 exhibits stable absorbency throughout the period worn.

In order to keep the base sheet 21 from exhibiting stretch property at the fixing points 33, the stretch property of the base sheet 21 may be eliminated, for example, by forming the fixing points 33 through ultrasonic embossing. Forming the fixing points 33 with an adhesive such as a hot melt adhesive also allows the stretch property of the base sheet 21 to be eliminated.

In cases where the base sheet 21 has stretch property, it is preferable that the fixing points 33 do not exhibit stretch property, as described above. In other words, it is preferable that only sections between the fixing points 33 exhibit stretch property in the base sheet 21. That is, when the base sheet 21 in its natural state (relaxed state) as shown in FIG. 19(a) is extended in its planar direction, only the sections between the fixing points 33 extend as shown in FIG. 19(b). Here, the absorbent members 30 do not deform in shape. When the extended state of the base sheet 21, which is in its extended state as shown in FIG. 19(b), is canceled, only the sections between the fixing points 33 contract, causing no deformation in the shape of the absorbent members 30. Since the base sheet 21 has such a stretch property, the absorbent core 10 is superior in adaptability to a wearer's body and conformability to a wearer's movement. Note that the extended and contracted states of the intermediate sheet 20 are omitted from FIGS. 19(a) and 19(b) for convenience' sake.

In cases where the base sheet 21 has stretch property, it is preferable that the topsheet 101 and the backsheet 102 of the absorbent article 100 also have stretch property. Further, as described above, it is preferable that the intermediate sheet 20 also has stretch property. In this way, the entire absorbent article 100 is provided with stretch property as a whole.

In the seventh embodiment shown in FIG. 20, an absorbent core 10 having a number of absorbent members 30 is disposed between a topsheet 101 and a backsheet 102. An intermediate sheet 20 is disposed between the absorbent core 10 and the backsheet 102. The upper surface of the intermediate sheet 20 and the lower surface of each absorbent member 30 are fixed together through a fixing point 33 in such a manner that the absorbent member 30 has an overhang 34 formed thereon. Further, a liquid-permeable base sheet 21 is disposed between the absorbent core 10 and the topsheet 101. A number of discretely and independently arranged second absorbent members 30' are located across the planar direction of the article 10 between the base sheet 21 and the topsheet 101. The second absorbent members 30' may be arranged according to the pattern shown in FIG. 2 or the pattern shown in FIG. 7. The lower surface of each second absorbent member 30' is fixed to the upper surface side of the base sheet 21 through a fixing point 33'. The second absorbent members 30' are fixed to the base sheet 21 in the same manner as the absorbent members 30 are fixed to the intermediate sheet 20. Further, the explanation on the absorbent members 30 applies as appropriate to the constituent material, shape, size, etc., of the second absorbent members 30'. Furthermore, the explanation on the sixth embodiment applies as appropriate to the base sheet 21. The upper surface side of the absorbent members 30 is not fixed to the lower surface side of the base sheet 21. Likewise, the upper surface side of the second absorbent members 30' is not fixed to the lower surface side of the topsheet 102. According to the present embodiment, the above-described advantage becomes even more significant in cases where the same type of sheet as the intermediate sheet 20 is used as the base sheet 21.

In the eighth embodiment shown in FIG. 21, an absorbent core 10 having a number of absorbent members 30 is disposed between a topsheet 101 and a backsheet 102. An intermediate sheet 20 is disposed between the absorbent core 10 and the backsheet 102. The upper surface of the intermediate sheet 20 and the lower surface of each absorbent member 30 are fixed together through a fixing point 33 in such a manner that the absorbent member 30 has an overhang 34 formed thereon. Further, a base sheet 21 is disposed between the intermediate sheet 20 and the topsheet 101. More specifically, the base sheet 21 is disposed between the number of absorbent members 30 and the topsheet 101. A number of discretely and independently arranged second absorbent members 30' are located across the planar direction of the article 10 between the base sheet 21 and the intermediate sheet 20 and are disposed in a non-opposing state with respect to the absorbent members 30. That is, the absorbent members 30 and the second absorbent members 30' are arranged in a mutually-nesting state. The upper surface of each second absorbent member 30' is fixed to the lower surface side of the base sheet 21 through a fixing point 33'. The second absorbent members 30' are fixed to the base sheet 21 in the same manner as the absorbent members 30 are fixed to the intermediate sheet 20. Further, the explanation on the absorbent members 30 applies as appropriate to the constituent material, shape, size, etc., of the second absorbent members 30'. Furthermore, the explanation on the foregoing embodiments applies as appropriate to the base sheet 21. The upper surface side of the absorbent members 30 is not fixed to the lower surface side of the base sheet 21. Likewise, the lower surface side of the second absorbent members 30' is not fixed to the upper surface side of the intermediate sheet 20.

In the embodiment shown in FIG. 21, a number of discretely and independently arranged third absorbent members 30" are also located across the planar direction of the article 100 between the base sheet 21 and the topsheet 101. That is, the second absorbent members 30' and the third absorbent members 30" are formed on the respective surfaces of the base sheet 21. The lower surface of the third absorbent members 30" is fixed to the upper surface side of the base sheet 21 through respective fixing points 33". Viewing the base sheet 21 from above, the positions of the second absorbent members 30' and the positions of the third absorbent members 30" differ from each other. The fixing points 33' and the fixing points 33" also differ in position. The third absorbent members 30" are fixed to the base sheet 21 in the same manner as the absorbent members 30 are fixed to the intermediate sheet 20. Further, the explanation on the absorbent members 30 applies as appropriate to the constituent material, shape, size, etc., of the third absorbent members 30".

The present embodiment is advantageous in that the liquid-absorption capacity can be increased. Also, the excreted high-viscosity fluid is absorbed and retained not only by the absorbent members 30 but also by the second absorbent members 30' and the third absorbent members 30". This allows the high-viscosity fluid to be trapped even more securely.

Figure 22:
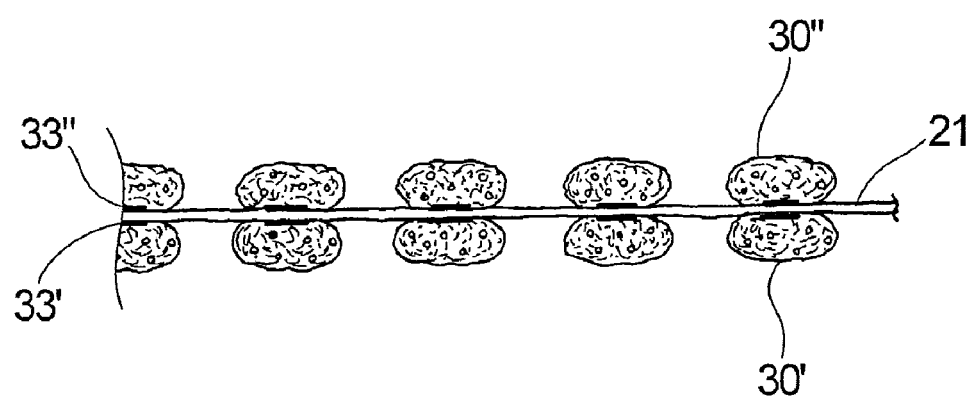
FIG. 22 is a schematic diagram showing another arrangement of second absorbent members and third absorbent members of the absorbent article according to the eighth embodiment of the present invention.

The embodiment shown in FIG. 22 is a modified example of the embodiment shown in FIG. 21. Like the embodiment shown in FIG. 21, the embodiment shown in FIG. 22 has second absorbent members 30' and third absorbent members 30" formed on the respective surfaces of the base sheet 21. Different from the embodiment shown in FIG. 21, however, the positions of the second absorbent members 30' coincide with the positions of the third absorbent members 30" in the present embodiment when viewing the base sheet 21 from above. Also, the fixing points 33' and the fixing points 33" coincide in position. The present embodiment also achieves the same effects as those of the embodiment shown in FIG. 21.

The positions of the second absorbent members 30' and the third absorbent members 30" of the embodiments shown in FIGS. 21 and 22 can be produced by using, in the method for producing the absorbent members 30 shown in FIGS. 8 to 11, a base sheet 21 in place of the intermediate sheet 20 and disposing fibrous sheets 300 on both sides of the base sheet 21. Further, the same pattern-indented roller as the first roller 401 may be used as the second roller 402 in the cutting device shown in FIG. 10(a).

Although the present invention has been described above according to preferred embodiments thereof, the invention is not to be limited to those embodiments. For example, in the embodiments shown in FIGS. 1, 12, 14, and 15, it is possible to dispose a fiber stack made of pulp, or a fiber stack made of pulp and superabsorbent polymer, right above the backsheet 102. Likewise, in the embodiments shown in FIGS. 16, 18, 20, and 21, it is possible to dispose a fiber stack made of pulp, or a fiber stack made of pulp and superabsorbent polymer, right above the backsheet 102.

EXAMPLES

The present invention is described in further detail below through examples. The scope of the present invention, however, is not limited by these examples.

Example 1 and Comparative Example 1

An absorbent article (absorbent pad) having the structure shown in FIG. 1 was prepared. The topsheet and the intermediate sheet, as well as the absorbent core and the backsheet, were fixed together by applying a hot melt adhesive in spiral patterns (basis weight: 10 g/m$^2$). The size of the absorbent article was 350 mm×110 mm.

As the topsheet, an air-through nonwoven fabric (basis weight: 10 g/m$^2$) including a sheath/core conjugate fiber made of 2.3 dtex polypropylene/high-density polyethylene (PP•HDPE) treated with hydrophilic agent (hydrophilic oil solution) was used. The absorption rate of physiological saline solution of the topsheet was 0.011 ml/(g·s). As the intermediate sheet, an air-through nonwoven fabric (basis weight: 80 g/m$^2$) obtained by heat-treating a side-by-side conjugate fiber made of 2.2 dtex polypropylene/polyethylene treated with hydrophilic agent (hydrophilic oil solution) was used. The absorption rate of physiological saline solution of the intermediate sheet was 0.115 ml/(g·s). As the backsheet, a liquid-impermeable polyethylene film (basis weight: 15 g/m$^2$) was used. As the absorbent core, a mixture containing a side-by-side conjugate fiber made of polypropylene/polyethylene, pulp, and absorbent polymer (basis weight of each component: 40, 200, and 50 g/m$^2$) was used, and the absorbent core was prepared by the method shown in FIG. 8. The absorption rate of physiological saline solution of the absorbent core was 1.20 ml/(g·s) The absorbent members of the absorbent core were fixed to the bottom of the nonwoven fabric serving as the intermediate sheet through ultrasonic embossing. Each absorbent member had the shape of a square 8 mm×8 mm in size as viewed from above, and the absorbent members were arranged in a staggered pattern across the entire surface of the intermediate sheet at 2 mm intervals. The absorbent article thus obtained was taken as Example 1. As Comparative example 1, an absorbent article was prepared with the intermediate sheet removed from Example 1 and the absorbent members fixed directly to the topsheet.

The absorbency of the absorbent articles according to Example 1 and Comparative example 1 was measured according to the following method using defibrinated horse blood. The results are shown in Table 1 below.

<Measurement Method>

Under a weight of 0.5 kPa, 6 g of defibrinated horse blood was injected at once into the central portion of the topsheet of the absorbent article at constant speed (6 seconds). The time required for absorbing the horse blood ("absorption time") in this procedure and the amount of blood remaining on the topsheet ("remaining amount on topsheet") were measured. Also, after leaving the absorbent article still for 3 minutes after finishing injection, 10 sheets of pulp paper (absorption paper) having a basis weight of 37 g/m$^2$ were placed on the topsheet under a weight of 5 kPa, and the amount of blood absorbed by the absorption paper ("absorption amount by absorption paper") was also measured.

TABLE 1

|  | Absorption time sec | Remaining amount on topsheet g | Absorption amount by absorption paper g |
|---|---|---|---|
| Example 1 | 7.8 | 0.29 | 1.38 |
| Comparative example 1 | 11.8 | 0.59 | 2.2 |

As shown in Table 1, the absorbent article according to Example 1 resulted in shorter absorption time and was improved in both "remaining amount on topsheet" and "absorption amount by absorption paper", compared to Comparative example 1. It was thus confirmed that disposing an intermediate sheet between the topsheet and the absorbent core allows liquid to be promptly drawn up from the topsheet and reduces both the amount of blood remaining on the topsheet and the absorption amount by the absorption paper, thereby improving dry feel.

Example 2 and Comparative Examples 3 and 4

An absorbent article (sanitary napkin) having the structure shown in FIG. 16 was prepared. The interface between the topsheet and the absorbent core, as well as the interface between the intermediate sheet and the backsheet, were fixed together by applying a hot melt adhesive in spiral patterns (basis weight: 10 g/m$^2$). The size of the absorbent article was 350 mm×110 mm.

The topsheet, the intermediate sheet, the backsheet, and the absorbent core used were the same as those of Example 1. Each absorbent member of the absorbent core was fixed on the top of the nonwoven fabric serving as the intermediate sheet through ultrasonic embossing. Each absorbent member had the shape of a square 8 mm×8 mm in size, and the absorbent members were arranged in a staggered pattern at 2 mm intervals. The obtained absorbent article was taken as Example 2. As Comparative example 3, an absorbent article was prepared with the intermediate sheet removed from Example 2 and the absorbent members fixed directly to the backsheet. Further, as Comparative example 4, an absorbent article was prepared using a mixture containing pulp and absorbent polymer (basis weight of each component: 300 and 300 g/m$^2$) in continuous form in place of the absorbent core used in Example 2.

The wet-back preventing property of the absorbent articles according to Example 2 and Comparative examples 3 and 4 was measured according to the following method. The results are shown in Table 2 below.

<Measurement Method>

Viscous fluid having a viscosity of 300 mPa·s (at 25° C. using a vibrating viscometer) was used as high-viscosity fluid serving as a model of artificial soft feces, and the amount of wet-back of the absorbent article was measured. Ten grams of artificial soft feces was injected at once from the topsheet side of the absorbent article at constant speed (6 seconds), and the article was left for 5 minutes under a weight of 3.5 kPa. In doing so, an OHP film was placed between the weight for applying the weight and the absorbent article. The amount of fluid attached to the OHP film was measured, and this amount was regarded as the "attachment amount to skin". The amount of fluid remaining on the topsheet ("remaining amount on topsheet") was also measured. The constituents of the viscous fluid were as follows: 28.0 g of bentonite; 14.0 g of glycerin; 114.1 g of ion-exchanged water; and 14.2 g of 0.03-percent-by-weight aqueous solution of EMULGEN 130K (from Kao Corporation).

TABLE 2

|  | Attachment amount to skin g | Remaining amount on topsheet g |
|---|---|---|
| Example 2 | 0.39 | 1.45 |
| Comparative example 3 | 0.60 | 2.00 |
| Comparative example 4 | 0.50 | 1.87 |

As shown in Table 2, the absorbent article according to Example 2 resulted in lower "attachment amount to skin" and "remaining amount on topsheet", compared to Comparative example 3. Also, Example 2 was reduced in both "attachment amount to skin" and "remaining amount on topsheet" compared to Comparative example 4. It was thus confirmed that by providing an intermediate sheet and separating the absorbent core into a plurality of absorbent members, the absorbency with respect to high-viscosity fluid is improved.

INDUSTRIAL APPLICABILITY

As described in detail above, according to the absorbent article of the present invention (preferably with the first to fourth embodiments), the intermediate sheet disposed on the absorbent member group functions to reduce the tendency for liquid to remain on portions of the topsheet where absorbent members are not located thereunder, and thus the topsheet is improved in dry feel. In addition, liquid once absorbed by the absorbent members is less prone to wet-back. Further, the spaces existing among the absorbent members work to improve the draping property of the article, and thus the article becomes less prone to creases and kinks while worn.

Further, according to the absorbent article of the present invention (preferably with the fifth to eighth embodiments), the intermediate sheet functions to diffuse, in the planar direction of the article, the liquid component of the high-viscosity fluid, such as soft feces, retained in the spaces among the absorbent members and also functions to allow the absorbent members to absorb the liquid component. Thus, soft feces can be dried easily. This results in making it difficult for wet-back to occur and improving the retainability of soft feces within the absorbent core. Further, forming the absorbent core with the absorbent member group including a number of discretely-and-independently arranged absorbent members improves the draping property of the article owing to the spaces existing among the absorbent members, and thus the article becomes less prone to creases and kinks while worn.

The invention claimed is:

1. An absorbent article comprising a topsheet that is adapted to be locate proximal to a wearer's skin, a backsheet that is adapted to be located distal to the wearer's skin, and an absorbent core disposed between the topsheet and the backsheet,
the absorbent core comprising a number of discretely and independently arranged absorbent members which are located across a planar direction of the article,
an intermediate sheet being disposed between the topsheet and the absorbent core or between the backsheet and the absorbent core,
the absorbent members being fixed to the intermediate sheet,
wherein the intermediate sheet is disposed between the backsheet and the absorbent core, and
wherein an absorption rate of physiological saline solution measured by D/W method of the intermediate sheet and the absorption rate of the absorbent core are higher than the absorption rate of the topsheet.

2. The absorbent article according to claim 1, wherein an absorption rate of physiological saline solution measured by D/W method of each of the topsheet, the intermediate sheet, and the absorbent core satisfies the following relationship:
the topsheet<the intermediate sheet<the absorbent core.

3. The absorbent article according to claim 1, wherein:
the intermediate sheet is disposed between the backsheet and the absorbent core, and
a liquid-permeable base sheet is disposed between the absorbent members and the topsheet.

4. The absorbent article according to claim 3, wherein the absorbent members are fixed to an upper surface side of the intermediate sheet and to a lower surface side of the base sheet.

5. The absorbent article according to claim 3, wherein the base sheet has stretch property.

6. The absorbent article according to claim 3, wherein:
a number of discretely and independently arranged second absorbent members are located across the planar direction of the article between the base sheet and the topsheet, and
the second absorbent members are fixed to an upper surface side of the base sheet.

7. The absorbent article according to claim 3, wherein:
a number of discretely and independently arranged second absorbent members are located across the planar direction of the article between the base sheet and the intermediate sheet in such a manner that the second absorbent members are disposed in a non-opposing state with respect to the absorbent members, and
the second absorbent members are fixed to a lower surface of the base sheet.

8. The absorbent article according to claim 7, wherein a number of discretely and independently arranged third absorbent members are located across the planar direction of the article between the base sheet and the topsheet.

9. The absorbent article according to claim 1, wherein:
the intermediate sheet is disposed between the topsheet and the absorbent core, and
a liquid-permeable base sheet is disposed between the absorbent members and the backsheet.

10. The absorbent article according to claim 9, wherein the absorbent members are fixed to a lower surface side of the intermediate sheet and to an upper surface of the base sheet.

11. The absorbent article according to claim 9, wherein the base sheet has stretch property.

12. The absorbent article according to claim 1, wherein:
the intermediate sheet is disposed between the topsheet and the absorbent core,
a liquid-permeable base sheet is disposed between the absorbent members and the backsheet,
a number of discretely and independently arranged second absorbent members are located across the planar direction of the article between the base sheet and the backsheet, and
the second absorbent members are fixed to a lower surface side of the base sheet.

13. The absorbent article according to claim 1, wherein:
the intermediate sheet is disposed between the topsheet and the absorbent core,
a liquid-permeable base sheet is disposed between the intermediate sheet and the backsheet, and
a number of discretely and independently arranged second absorbent members are located across the planar direction of the article between the base sheet and the intermediate sheet in such a manner that the second absorbent members are disposed in a non-opposing state with respect to the absorbent members.

* * * * *